(12) United States Patent
Friesen et al.

(10) Patent No.: US 6,204,275 B1
(45) Date of Patent: Mar. 20, 2001

(54) PDE IV INHIBITING COMPOUNDS, COMPOSITIONS AND METHODS OF TREATMENT

(75) Inventors: Richard Friesen; Yvbes Ducharme; Daniel Dube; Yves Girard; Richard Frenette; Chun Li; Marc Blouin; Nathalie Chauret; Laird Trimble, all of Quebec (CA)

(73) Assignee: Merck Frosst Canada & Co., Kirkland (CA)

( * ) Notice: Subject to any disclaimer, the term of this patent is extended or adjusted under 35 U.S.C. 154(b) by 0 days.

(21) Appl. No.: 09/513,149

(22) Filed: Feb. 25, 2000

Related U.S. Application Data

(60) Provisional application No. 60/121,530, filed on Feb. 25, 1999, and provisional application No. 60/160,370, filed on Oct. 19, 1999.

(51) Int. Cl.[7] ........................ C07D 401/02; A61K 31/44
(52) U.S. Cl. ............................ 514/332; 546/266
(58) Field of Search ............... 546/266; 514/332

(56) References Cited

U.S. PATENT DOCUMENTS

| | | | |
|---|---|---|---|
| 4,166,452 | 9/1979 | Generales, Jr. ................ | 128/741 |
| 4,256,108 | 3/1981 | Theeuwes ..................... | 128/260 |
| 4,265,874 | 5/1981 | Bonsen et al. ................. | 424/15 |
| 5,622,977 | 4/1997 | Warrellow et al. ............. | 514/336 |
| 5,710,170 | 1/1998 | Guay et al. .................... | 514/332 |

FOREIGN PATENT DOCUMENTS

WO91/16457   10/1991   (CA) .

OTHER PUBLICATIONS

Beavo, et al., Trends in Pharmacological Sciences, 11:150–155 (1990).
Nicholson, et al., Trends in Pharmacological Sciences, 12:19–27 (1991).
Torphy, et al., Thorax, 46:512–523 (1991).
P.T. Peachell, et al., J. Immunol., 148:2503–2510 (1992).
G. Dent, et al., Br. J. Pharmacol., 103:1339–1346 (1991).
J.V. Swinnen, et al., Proc. Natl. Acad. Sci. USA, 86:5325–5329 (1989).
G. Bolger, et al., Mol. Cell. Biol., 13:6558–6571 (1993).
R. Obermolte, et al., Gene, 129:239–247 (1993).
M. Mclaughlin, et al., J. Biol. Chem., 268:6470–6476 (1993).
R. Davis, et al., Proc. Natl. Acad. Sc. USA, 86:3604–3608 (1989).
J.V. Swinnen, et al., J. Biol. Chem., 266:18370–18377 (1991).

*Primary Examiner*—Zinna Northington Davis
(74) *Attorney, Agent, or Firm*—Shu M. Lee; David L. Rose

(57) ABSTRACT

The invention encompasses compounds of Formula I useful in the treatment of diseases, including asthma, by raising the level of cyclic adenosine-3',5'-monophosphate (cAMP) through the inhibition of phosphodiesterase IV (PDE IV).

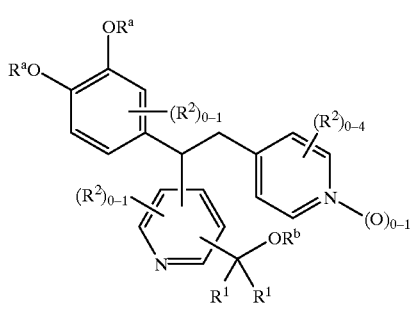

The invention also encompasses certain pharmaceutical compositions and methods for treatment of diseases by inhibition of PDE IV, resulting in an elevation of cAMP, comprising the use of compounds of Formula I.

22 Claims, No Drawings

PDE IV INHIBITING COMPOUNDS, COMPOSITIONS AND METHODS OF TREATMENT

This application claims the benefit of priority to Provisional Application No. 60/121,530 filed Feb. 25, 1999 and Provisional Application No. 60/160,370 filed Oct. 19, 1999.

BACKGROUND OF THE INVENTION

This invention relates to compounds and pharmaceutical compositions for the treatment of diseases by raising the level of cyclic adenosine-3',5'-monophosphate (cAMP) through the inhibition of phosphodiesterase IV (PDE IV).

Many hormones and neurotransmitters modulate tissue function by elevating intracellular levels of 3',5'-cyclic adenosine monophosphate (cAMP). The cellular levels of cAMP are regulated by mechanisms which control synthesis and breakdown. The synthesis of cAMP is controlled by adenyl cyclase which may be directly activated by agents such as forskolin or indirectly activated by the binding of specific agonists to cell surface receptors which are coupled to adenyl cyclase. The breakdown of cAMP is controlled by a family of phosphodiesterase (PDE) isoenzymes, which also control the breakdown of guanosine 3',5'-cyclic monophosphate (cGMP). At least seven members of the family have been described (PDE I-VII), the distribution of which varies from tissue to tissue. This suggests that specific inhibitors of PDE isoenzymes could achieve differential elevation of cAMP in different tissues [for reviews of PDE distribution, structure, function and regulation, see Beavo & Reifsnyder (1990) TIPS, 11:150–155, Nicholson et. al. (1991) TIPS, 12: 19–27, and Torphy and Undem (1991) Thorax, 46: 512–523].

The availability of PDE isotype selective inhibitors has enabled the role of PDEs in a variety of cell types to be investigated. In particular it has been established that PDE IV controls the breakdown of cAMP in many inflammatory cells, for example, basophils (Peachell P. T. et al., (1992) J. Immunol., 148: 2503–2510) and eosinophils (Dent G. et al., (1991) Br. J. Pharmacol., 103: 1339–1346) and that inhibition of this isotype is associated with the inhibition of cell activation. Furthermore, elevation of cAMP in airway smooth muscle has a spasmolytic effect. Consequently PDE IV inhibitors are currently being developed as potential anti-inflammatory drugs particularly for the prophylaxis and treatment of asthma, by achieving both anti-inflammatory and bronchodilator effects.

The application of molecular cloning to the study of PDEs has revealed that for each isotype there may be one or more isoforms. PDE IV has been shown to exist in four isoforms (A, B, C and D) to date, each coded for by a separate gene in both rodents (Swinnen J. V. et al., (1989) Proc. Natl. Acad. Sci. USA, 86: 5325–5329) and man (Bolger G. et al., (1993) Mol. Cell Biol., 13: 6558–6571).

The existence of multiple PDE IVs raises the prospect of obtaining inhibitors that are selective for individual isoforms, thus increasing the specificity of action of such inhibitors. This assumes that the different PDE IV isoforms are functionally distinct. Indirect evidence in support of this comes from the selective distribution of these isoforms in different tissues (Swinnen et al., 1989; Bolger et al., 1993; Obernolte R. et al., (1993) Gene, 129: 239–247, ibid) and the high degree of sequence conservation amongst isoforms of different species.

To date, full length cDNAs for human PDE IVA, B and D (Bolger et al., 1993 ibid; Obernolte et al., 1993 ibid; Mclaughlin M. et al., (1993) J. Biol. Chem., 268: 6470–6476) and rat PDE IVA, B and D (Davis R. et al., (1989) Proc. Natl. Acad. Sci. USA, 86: 3604–3608; Swinnen J. V. et al., (1991) J. Biol. Chem., 266: 18370–18377), have been reported, enabling functional recombinant enzymes to be produced by expression of the cDNAs in an appropriate host cell. These cDNAs have been isolated by conventional hybridization methods. However using this approach, only partial cDNAs for both human and rat PDE IVC have been obtained. (Bolger et al., ibid. 1993 and Swinnen et al., ibid. 1989 and International Patent Specification No. WO 91/16457.)

The design of PDE IV inhibitors for the treatment of inflammatory diseases such as asthma, has met with limited success to date. Many of the PDE IV inhibitors which have been synthesised have lacked potency and/or inhibit more than one type of PDE isoenzyme in a non-selective manner. PDE IV inhibitors that are relatively potent and selective for PDE IV, are reported to be emetic as well. Indeed this side effect has been so universal that experts have expressed their belief that the emesis experienced upon administration of a PDE IV inhibitor may be mechanism based.

The compounds described herein are potent inhibitors of PDE TV at concentrations that exhibit little or no inhibitory action on other PDE isoenzymes. These compounds inhibit the human recombinant PDE IV enzyme and also elevate cAMP in isolated leukocytes. Certain compounds prevent inflammation in the lungs induced by carrageenan, platelet-activating factor (PAF), interleukin-5 (IL-5) or antigen challenge. These compounds also suppress the hyperresponsiveness of airway smooth muscle seen in inflamed lungs. Advantageously, compounds according to the invention have good oral activity, and at orally effective doses exhibit little or none of the side-effects associated with known PDE IV inhibitors, such as rolipram. The compounds of the invention are therefore of use in medicine, especially in the prophylaxis and treatment of asthma and other inflammatory conditions.

SUMMARY OF THE INVENTION

A compound represented by formula I:

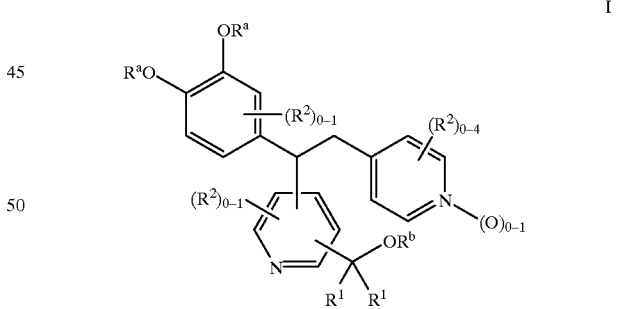

or a pharmaceutically acceptable salt thereof wherein:

each $R^a$ independently represents a member selected from the group consisting of: H, $C_{1-6}$alkyl and halo$C_{1-6}$alkyl;

$R^b$ represents a member selected from the group consisting of: H, $C_{1-6}$alkyl, halo$C_{1-6}$alkyl;

each $R^1$ independently represents a member selected from the group consisting of: $C_{1-10}$alkyl, aryl, heteroaryl, substituted $C_{1-10}$alkyl, substituted aryl and substituted heteroaryl, wherein the substituents are 1–6 members selected from the group consisting of: $C_{1-4}$alkyl, halo, hydroxy, halo$C_{1-4}$alkyl, CN, $C_{1-4}$alkoxy, $C_{1-4}$alkylthio, $C_{1-4}$alkyl-$SO_2$— and $H_2NSO_2$—; and when present, each $R^2$ independently represents a member selected from the group consisting of: halo, $C_{1-6}$alkyl, halo$C_{1-6}$alkyl and CN.

DETAILED DESCRIPTION OF THE INVENTION

The terms used herein have the following meanings unless otherwise indicated.

Heteroaryl is a member selected from the group consisting of pyridyl and thiazolyl.

Halo includes F, Cl, Br and I.

Alkyl and the alkyl portion of alkoxy include linear, branched and cyclic structures, with the indicated number of carbon atoms. Thus, examples of $C_{1-6}$alkyl include methyl, ethyl, propyl, 2-propyl, s- and t-butyl, butyl, pentyl, hexyl, 1,1-dimethylethyl, cyclopropyl, cyclobutyl, cyclopentyl and cyclohexyl. Similarly, $C_{1-6}$alkoxy is intended to include alkoxy groups of from 1 to 6 carbon atoms of a straight, branched, or cyclic configuration. Examples of alkoxy groups include methoxy, ethoxy, propoxy, isopropoxy, cyclopropyloxy, cyclohexyloxy, and the like. Likewise, $C_{1-6}$alkylthio is intended to include alkylthio groups of from 1 to 6 carbon atoms of a straight, branched or cyclic configuration. Examples of alkylthio groups include methylthio, propylthio, isopropylthio, cycloheptylthio, etc. By way of illustration, the propylthio group signifies —SCH$_2$CH$_2$CH$_3$.

Halo$C_{1-6}$alkyl means an alkyl group in which one or more hydrogen atoms have been replaced by halogen atoms, with up to complete substitution of all hydrogen atoms with halo groups, e.g., —CF$_3$, —CF$_2$CF$_3$ and the like.

The invention encompasses compounds of Formula I useful in the treatment of disease by inhibition of PDE IV:

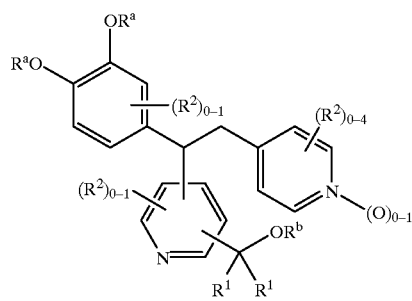

I or a pharmaceutically acceptable salt thereof wherein:

each $R^a$ independently represents a member selected from the group consisting of: H, $C_{1-6}$alkyl and halo$C_{1-6}$alkyl;

$R^b$ represents a member selected from the group consisting of: H, $C_{1-6}$alkyl, halo$C_{1-6}$alkyl;

each $R^1$ independently represents a member selected from the group consisting of: $C_{1-10}$alkyl, aryl, heteroaryl, substituted $C_{1-10}$alkyl, substituted aryl and substituted heteroaryl, wherein the substituents are 1–6 members selected from the group consisting of: $C_{1-4}$alkyl, halo, hydroxy, halo$C_{1-4}$alkyl, CN, $C_{1-4}$alkoxy, $C_{1-4}$alkylthio, $C_{1-4}$alkyl-SO$_2$— and H$_2$NSO$_2$—; and when present, each $R^2$ independently represents a member selected from the group consisting of: halo, $C_{1-6}$alkyl, halo$C_{1-6}$alkyl and CN.

A subset of compounds of the invention is represented by Formula Ia:

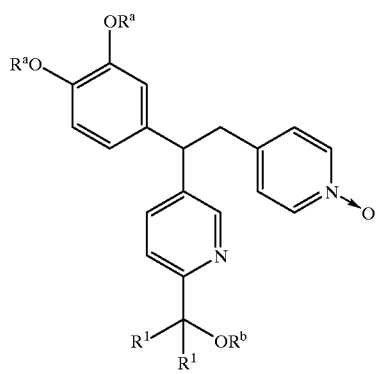

Ia

Within this subset, all variables are as originally defined.

Another subset of compounds that is of particular interest is represented by formula I or Ia wherein each $R^a$ represents difluoromethyl and $R^b$ represents H. Within this subset, all variables are as originally defined.

Another subset of compounds that is of particular interest is represented by formula I or Ia wherein one $R^1$ group represents alkyl and the other represents aryl or substituted aryl. Within this subset, all variables are as originally defined.

Still another subset of compounds that is of particular interest is represented by formula I or Ia wherein one $R^a$ group represents cycloalkoxy and each $R^1$ represents methyl.

Preferred values of $R^a$ are i) halo$C_{1-6}$alkyl groups selected from CH$_3$, CH$_2$F, CHF$_2$ and CF$_3$, most preferably CHF$_2$; and ii) cycloalkoxy, more preferably cyclobutyloxy and cyclopropyloxy.

The preferred value of $R^b$ is H.

Preferred values of $R^1$ are alkyl, substituted alkyl, aryl, substituted aryl and heteroaryl. Preferred alkyl groups include methyl, ethyl, n-propyl, isopropyl, n-butyl, isobutyl and cyclohexyl. Preferred substituted alkyl groups include haloalkyl, such as CF$_3$. Preferred aryl and substituted aryl groups include, respectively, phenyl and phenyl substituted with halo, e.g., Cl or F, alkyl, e.g., methyl and ethyl, and alkylsulfonyl, e.g., MeSO$_2$—. The preferred heteroaryl group is thiazolyl.

Preferred compounds of formula I are in the form of the pyridyl-N-oxide.

Representative examples of compounds of the invention include the following:

(a) (±)-4-{2-[3,4-Bis(difluoromethoxy)phenyl]-2-{5-[2-(1-hydroxy-1-methyl)ethyl]pyridyl}ethyl}pyridine N-oxide, (b and c) Optical isomers of 4-{2-[3,4-Bis (difluoromethoxy)phenyl]-2-{5-[2-(1-hydroxy-1-methyl) ethyl]pyridyl}ethyl}pyridine N-oxide, (d) (±)-4-{2-[3,4-Bis(difluoromethoxy)phenyl]-2-{5-[2-(1-ethyl-1-hydroxy)propyl]pyridyl}ethyl}pyridine N-oxide, (e) (±/±)-4-{2-[3,4-Bis(difluoromethoxy)phenyl]-2-{5-[2-(1-hydroxy-1-isobutyl)ethyl]pyridyl}ethyl}pyridine N-oxide, (f) (±/±)-4-{2-[3,4-Bis(difluoromethoxy)phenyl]-2-{5-[2-(1-hydroxy-1-isobutyl)trifluoroethyl] pyridyl}ethyl}pyridine N-oxide, (g) (±/±)-4-{2-[3,4-Bis(difluoromethoxy)phenyl]-2-{5-[2-(1-hydroxy-1-methyl)pentyl]pyridyl) ethyl}pyridine N-oxide, (h) (±/±)-4-{2-[3,4-Bis(difluoromethoxy)phenyl]-2-{5-[2-(1-cyclohexyl-1-hydroxy)ethyl]pyridyl}ethyl}pyridine N-oxide, (i) (±/±)-4-{2-[3,4-Bis(difluoromethoxy)phenyl]-2-{5-[2-(1-cyclohexyl-1-hydroxy)trifluoroethyl]pyridyl}ethyl}pyridine N-oxide, (j) (±/±)-4-{2-[3,4-Bis(difluoromethoxy)phenyl]-2-{5-[2-(1-hydroxy-1-phenyl)ethyl]pyridyl}ethyl}pyridine N-oxide, (k,l and m) Optical isomers of 4-{2-[3,4-Bis(difluoromethoxy)phenyl]-2-{5-[2-(1-hydroxy-1-phenyl)ethyl]pyridyl}ethyl}pyridine N-oxide, (n) (±/±)-4-{2-[3,4-Bis(difluoromethoxy)phenyl]-2-{5-[2-(1-hydroxy-1-phenyl)trifluoroethyl]pyridyl}ethyl}pyridine N-oxide, (o) (±/±)-4-{2-[3,4-Bis(difluoromethoxy)phenyl]-2-{5-[2-(1-hydroxy-1-phenyl)propyl]pyridyl}ethyl}pyridine N-oxide, (p) (±/±)-4-{2-[3,4-Bis(difluoromethoxy)phenyl]-2-{5-[2-(1-hydroxy-1-phenyl-2-methyl)propyl]pyridyl}ethyl}pyridine N-oxide, (q) (±)-4-{2-[3,4-Bis(difluoromethoxy)phenyl]-2-[5-(2-diphenylcarbinol)pyridyl]ethyl}pyridine N-oxide, (r) (±/±)-4-{2-[3,4-Bis(difluoromethoxy)phenyl]-2-{5-[2-(1-hydroxy-1-(3-fluorophenyl))ethyl]pyridyl}ethyl}pyridine N-oxide, (s) (±/±)-4-{2-[3,4-Bis(difluoromethoxy)phenyl]-2-{5-[2-(1-hydroxy-1-(4-fluorophenyl))ethyl]pyridyl}ethyl}pyridine N-oxide, (t) (±/±)-4-{2-[3,4-Bis(difluoromethoxy)phenyl]-2-{5-[2-(1-hydroxy-1-(4-chlorophenyl))ethyl]pyridyl}ethyl}pyridine N-oxide, (u to x) Optical isomers of 4-{2-[3,4-Bis(difluoromethoxy)phenyl]-2-{5-[2-(1-hydroxy-1-(4-chlorophenyl))ethyl]pyridyl}ethyl}pyridine N-oxide, (y) (±/±)-4-{2-[3,4-Bis(difluoromethoxy)phenyl]-2-{5-[2-(1-hydroxy-1-(2-methylphenyl))trifluoroethyl]pyridyl}ethyl}pyridine N-oxide, (z) (±/±)-4-{2-[3,4-Bis(difluoromethoxy)phenyl]-2-{5-[2-(1-hydroxy-1-(3-methylphenyl))trifluoroethyl]pyridyl}ethyl}pyridine N-oxide, (aa) (±/±)-4-{2-[3,4-Bis(difluoromethoxy)phenyl]-2-{5-[2-(1-hydroxy-1-(4-methylphenyl))trifluoroethyl]pyridyl}ethyl}pyridine N-oxide, (bb) (±/±)-4-2-[3,4-Bis(difluoromethoxy)phenyl]-2-{5-[2-(1-hydroxy-1-(4-ethylphenyl))trifluoroethyl]pyridyl}ethyl}pyridine N-oxide, (cc) (±/±)-4-{2-[3,4-Bis(difluoromethoxy)phenyl]-2-{5-[2-(1-hydroxy-1-(4-methylsulfonylphenyl))ethyl]pyridyl}ethyl}pyridine N-oxide, (dd) (±/±)-4-{2-[3,4-Bis(difluoromethoxy)phenyl]-2-{5-[2-(1-hydroxy-1-(2-thiazolyl))ethyl]pyridyl}ethyl}pyridine N-oxide, (ee) (±/±)-4-{2-[3,4-Bis(difluoromethoxy)phenyl]-2-{5-[2-(1-hydroxy-1-(2-thiazolyl))trifluoroethyl]pyridyl}ethyl}pyridine N-oxide, (ff) chiral 4-{2-[(3-Cyclobutyloxy-4-difluoromethoxy)phenyl]-2-{5-[2-(1-hydroxy-1-methyl)ethyl]pyridyl}ethyl}pyridine N-oxide, and (gg) chiral-4-{2-[(3-Cyclopropyloxy-4-difluoromethoxy)phenyl]-2-{5-[2-(1-hydroxy-1-methyl)ethyl]pyridyl}ethyl}pyridine-N-oxide.

In another embodiment, the invention encompasses a pharmaceutical composition comprised of a compound of formula I in combination with a pharmaceutically acceptable carrier.

Within this embodiment, the invention encompasses pharmaceutical compositions for the treatment or prevention of diseases or conditions benefited by the inhibition of PDE IV, resulting in an elevation of cAMP, comprising a pharmaceutically acceptable carrier and a non-toxic therapeutically effective amount of compound of Formula I as described above.

The pharmaceutical compositions of the present invention comprise a compound of Formula I as an active ingredient or a pharmaceutically acceptable salt, thereof, and also contain a pharmaceutically acceptable carrier and optionally other therapeutic ingredients.

The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N__-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

The compounds described herein contain one or more asymmetric centers and thus give rise to diastereomers and optical isomers. The present invention includes all such possible diastereomers as well as their racemic and resolved, enantiomerically pure forms and pharmaceutically acceptable salts thereof.

It will be understood that in the discussion of methods of treatment which follows, references to the compounds of Formula I is meant to include pharmaceutically acceptable salts.

Compounds according to the invention are selective and potent inhibitors of PDE IV. The ability of the compounds to act in this way may be determined by the tests described in the Examples hereinafter.

The compounds according to the invention are thus of particular use in the prophylaxis and treatment of human diseases where an unwanted inflammatory response or muscular spasm (for example bladder or alimentary smooth muscle spasm) is present and where the elevation of cAMP levels may be expected to prevent or alleviate the inflammation and relax muscle.

Particular uses to which the compounds of the invention may be put include the prophylaxis and treatment of asthma, especially inflamed lung associated with asthma, cystic fibrosis, or in the treatment of inflammatory airway disease, chronic bronchitis, eosinophilic granuloma, psoriasis and other benign and malignant proliferative skin diseases, endotoxic shock, septic shock, ulcerative colitis, Crohn's disease, reperfusion injury of the myocardium and brain, inflammatory arthritis, chronic glomerulonephritis, atopic dermatitis, urticaria, adult respiratory distress syndrome, diabetes, diabetes insipidus, allergic rhinitis, allergic conjunctivitis, vernal conjunctivitis, arterial restenosis and atherosclerosis.

Compounds of the invention also suppress neurogenic inflammation through elevation of cAMP in sensory neurons. They are, therefore, analgesic, antitussive and antihyperalgesic in inflammatory diseases associated with irritation and pain.

Compounds of the invention also elevate cAMP in lymphocytes and thereby suppress unwanted lymphocyte activation in immune-based diseases such as rheumatoid arthritis, ankylosing spondylitis, transplant rejection and graft versus host disease.

Compounds of the invention also reduce gastric acid secretion and therefore can be used to treat conditions associated with hypersecretion of gastric acid.

Compounds of the invention suppress cytokine synthesis by inflammatory cells in response to immune or infectious stimulation. They are, therefore, useful in the treatment of bacterial, fungal or viral induced sepsis and septic shock in which cytokines such as tumour necrosis factor (TNF) are key mediators. Also compounds of the invention suppress inflammation and pyrexia due to cytokines and are, therefore, useful in the treatment of inflammation and cytokine-mediated chronic tissue degeneration which occurs in diseases such as rheumatoid or osteoarthritis.

Over-production of cytokines such as TNF in bacterial, fungal or viral infections, or in diseases such as cancer, leads to cachexia and muscle wasting. Compounds of the invention ameliorate these symptoms with a consequent enhancement of quality of life.

Compounds of the invention also elevate cAMP in certain areas of the brain and thereby counteract depression and memory impairment.

Compounds of the invention suppress cell proliferation in certain tumor cells and can be used, therefore, to prevent tumor growth and invasion of normal tissues.

For the prevention, prophylaxis or treatment of disease, the compounds may be administered to a mammalian patient in need of such prevention, prophylaxis or treatment, in an amount that is effective for preventing, controlling or treating the disease. In addition to the treatment of warm-blooded animals such as mice, rats, horses, cattle sheep, dogs, cats, etc., the compounds of the invention are effective in the treatment of humans.

The compounds of Formula I may be administered orally, topically, parenterally, by inhalation spray or rectally in the form of a pharmaceutical composition as described herein.

The term parenteral as used herein includes subcutaneous, intravenous, intramuscular or intrasternal injection or infusion techniques.

The pharmaceutical composition containing the active ingredient may be in a form suitable for oral use, for example, as tablets, troches, lozenges, aqueous or oily suspensions, dispersible powders or granules, emulsions, hard or soft capsules, syrups or elixirs. Compositions intended for oral use may be prepared according to any method known in the art for the manufacture of pharmaceutical compositions, and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or an oil medium, for example peanut oil, liquid paraffin or olive oil.

Aqueous suspensions contain the active material in admixture with excipients suitable for the manufacture of aqueous suspensions. Such excipients are suspending agents, for example sodium carboxymethyl-cellulose, methylcellulose, hydroxy-propylmethycellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Examples of such materials include cocoa butter and polyethylene glycols.

For topical use, creams, ointments, jellies, solutions or suspensions, etc., containing the compound of Formula I are employed. (For purposes of this application, topical application shall include mouth washes and gargles.)

Dosage levels of the order of from about 0.01 mg to about 140 mg/kg of body weight per day are useful in the treatment of the above-indicated conditions, or alternatively about 0.5 mg to about 7 g per patient per day. For example, inflammation may be effectively treated by the administration of from about 0.01 to 50 mg of the compound per kilogram of body weight per day, or alternatively about 0.5 mg to about 3.5 g per patient per day.

The amount of active ingredient that may be combined with the carrier materials to produce a single dosage form will vary depending upon the host treated and the particular mode of administration. For example, a formulation intended for the oral administration to humans may contain from about 0.5 mg to about 5 g of active agent compounded with an appropriate and convenient amount of carrier material which may vary from about 5 to about 95 percent of the total composition. Unit dosage forms will generally contain between from as low as about I mg to as high as about 1500 mg of an active ingredient, typically 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

Methods of Synthesis

The compounds of Formula I of the present invention can be prepared according to the synthetic routes outlined in Schemes I to IV and by following the methods described herein. It is obvious to one skilled in the art that resolution of compounds bearing stereogenic centers, such as VI to XVI, or compounds of Formula I, can be accomplished by one of several methods, including HPLC with a chiral column, or formation and crystallization of a salt prepared by reaction of the compound with a chiral acid or base. While the schemes show $R^2$ to be present, the $R^2$ groups can be readily omitted by modifying the starting compounds shown in Scheme 1.

Scheme 1

Compounds of Formula I may be prepared by the method presented in Scheme 1 from an appropriately substituted benzaldehyde II. Addition of an metalated bromopyridine, prepared by regioselective metalation of a dibromopyridine in a suitable solvent such as ether, THF or toluene, to II provides secondary alcohol III. Conversion of III into the corresponding chloride IV is accomplished by reaction with an appropriate chlorinating reagent such as thionyl chloride in an organic solvent such as dichloromethane. Alkylation of the anion derived from deprotonation of alkyl 4-pyridylacetate with an appropriate base, such as lithium or potassium bis(trimethylsilyl)amide, with the chloride IV in an appropriate organic solvent such as THF or HMPA, provides the ester V. Ester V is decarboxylated to give the bis-pyridine VI, first by heating in the presence of aqueous hydroxide, such as sodium hydroxide, in a mixture of protic and aprotic organic solvents, such as methanol or ethanol and THF, followed by acidification with mineral acid, such a hydrochloric acid. Reaction of the bromide VI with a metalated ethylene, such as vinyltributylstannane, in the presence of a catalytic amount of a palladium complex, such as bis(triphenylphosphine)palladium dichloride or dibromide, in an appropriate organic solvent, such as dioxane or THF, affords pyridine VII. Ozonolysis of the double bond, followed by reduction of the intermediate ozonide with an appropriate reducing agent, such as dimethylsulfide, provides the aldehyde VIII. Addition of an organometallic reagent, such as a Grignard reagent, to VIII in an appropriate organic solvent, such as ether, THF or dichloromethane, affords the secondary alcohol IX that can be oxidized by reaction with an oxidizing agent, such as manganese dioxide or oxalyl chloride/dimethylsulfoxide/triethylamine (Swern reagent), providing the ketone X. Addition of a second organometallic reagent, such as a Grignard reagent or an organolithium reagent, to X in an appropriate organic solvent, such as ether, THF or dichloromethane, gives the tertiary alcohol XI (pyridine of Formula I). Reaction of XI with an oxidizing agent, such as m-CPBA or MMPP provides the N-oxides of Formula I of the present invention.

Scheme 2

Alternatively, compounds of Formula I can be prepared using the route described in Scheme 2. Pyridyl ketone X can be oxidized by reaction with an oxidizing agent, such as m-CPBA or MMPP to provide the N-oxides XII. Addition of an organometallic reagent, such as a Grignard reagent or an organolithium reagent, to XII in an appropriate organic solvent, such as ether, THF or dichloromethane, gives compounds of Formula I of the present invention.

Scheme 3

Alternatively, ketones of structure X can be prepared using the route described in Scheme 3. Carbonylation of bromopyridine VI by reaction with carbon monoxide in the presence of a palladium catalyst, such as palladium acetate/dppf, and an alcohol, such as methanol, in an appropriate organic solvent, such as DMF, provides the pyridyl ester XIII. Conversion of the ester XIII into the Weinreb amide XIV is accomplished by reaction with a metalated methoxymethylamine, such as lithium or magnesium methoxymethylamine, in an appropriate organic solvent such as THF at low temperature. Addition of an organometallic reagent, such as a Grignard reagent or an organolithium reagent, to XIV in an appropriate organic solvent, such as ether or THF, gives ketone X.

Scheme 4

Compounds of Formula I in which $R^1$ are the same substitutent, can be prepared using the routes described in Scheme 4. Addition of excess of an organometallic reagent, such as a Grignard reagent or an organolithium reagent, to XIII in an appropriate organic solvent, such as ether, THF or dichloromethane, gives tertiary alcohol XV (pyridine of Formula I). Reaction of XV with an oxidizing agent, such as m-CPBA or MMPP provides the N-oxides of Formula I of the present invention. Alternatively, treatment of ester XIII with an oxidizing agent, such as m-CPBA or MMPP provides the N-oxide XVI. Addition of excess of an organometallic reagent, such as a Grignard reagent or an organolithium reagent, to XIII in an appropriate organic solvent, such as ether, THF or dichloromethane, gives compounds of Formula I of the present invention.

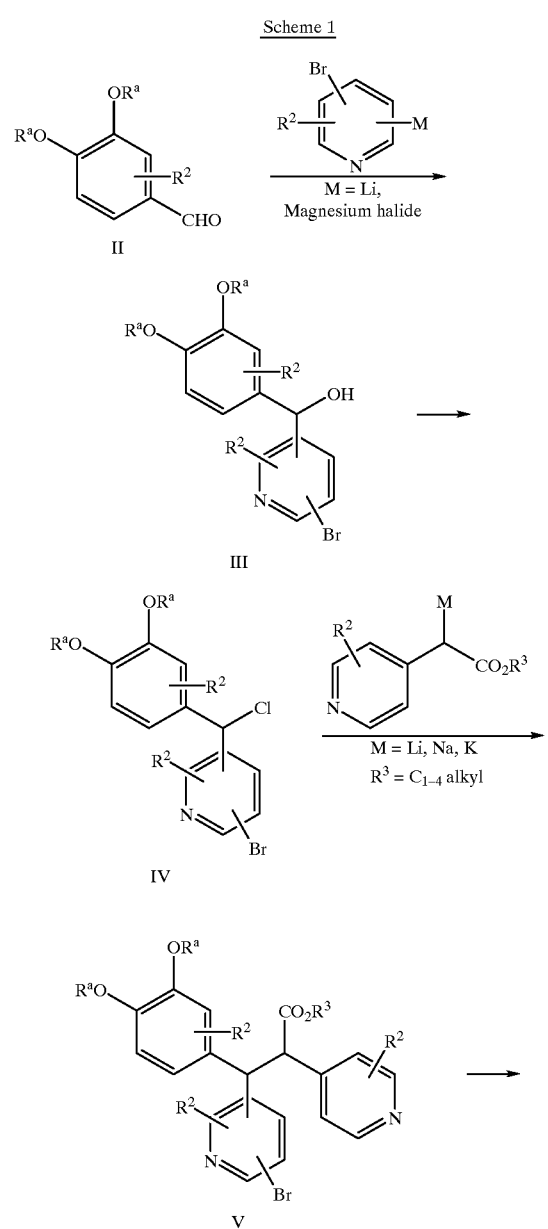

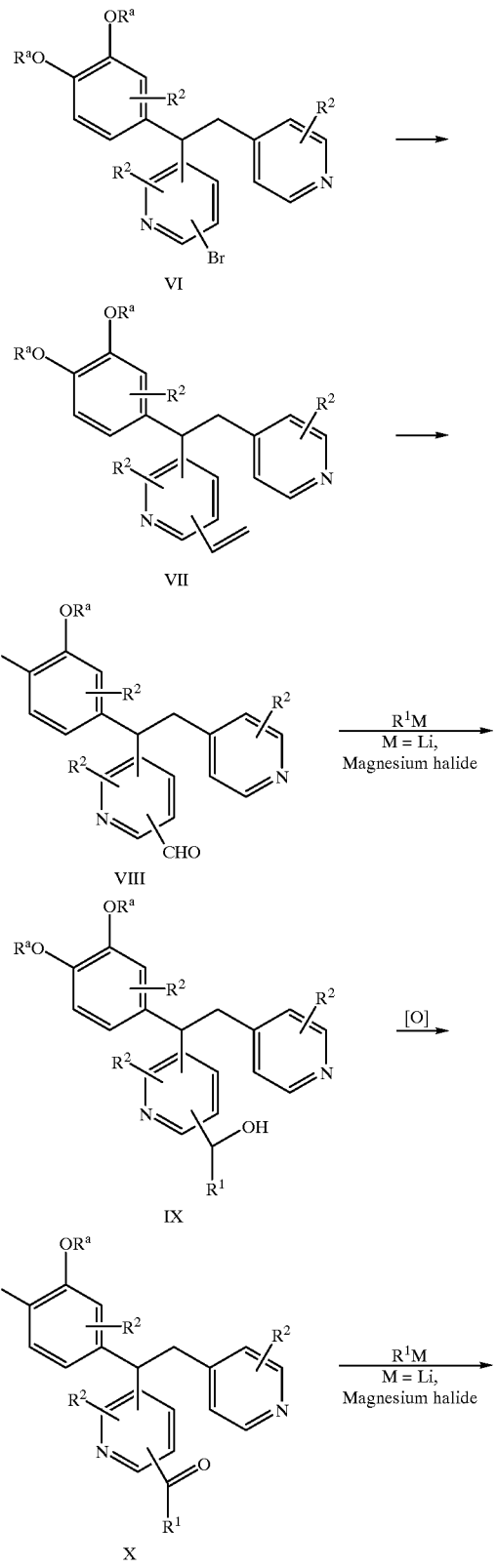

-continued
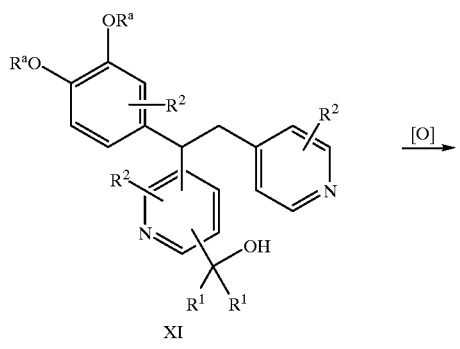
XI
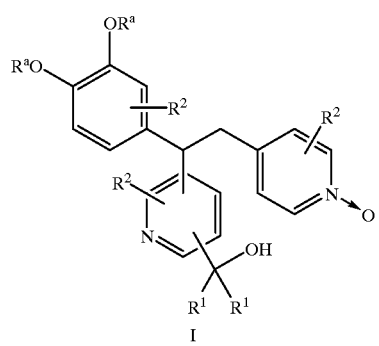
I
Scheme 2
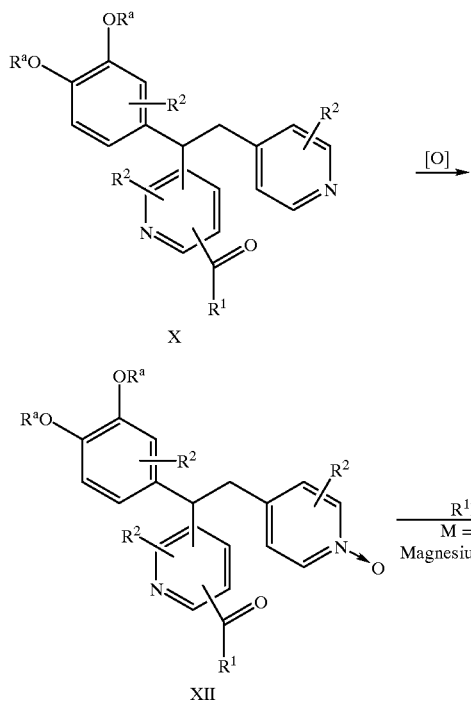
XII
Scheme 3
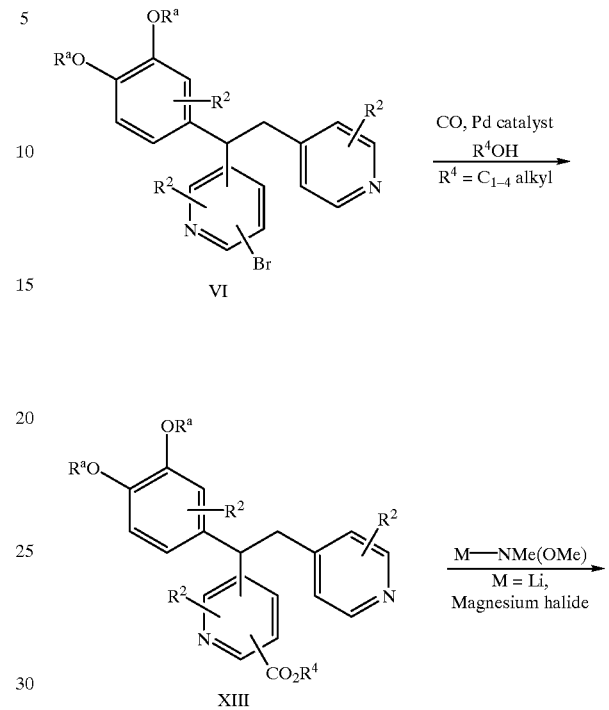
VI
XIII
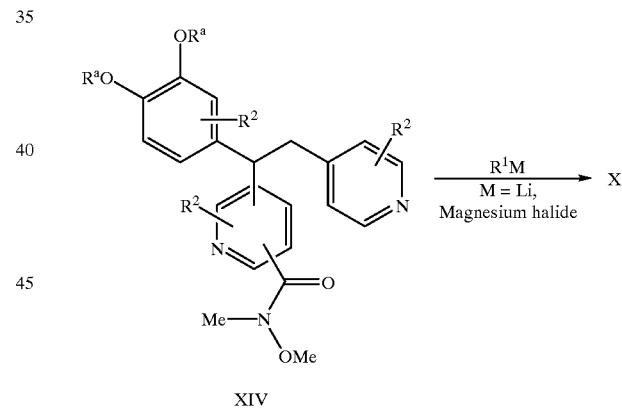
XIV

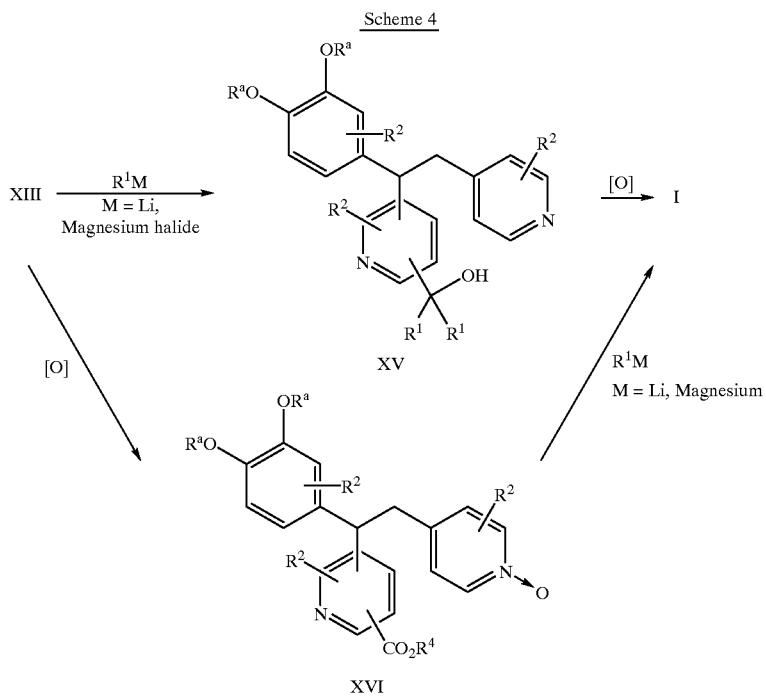

Representative compounds are shown in Table 1.

TABLE 1

Ib

| Example | R$^{1a}$ | R$^{1b}$ |
|---|---|---|
| 1 | CH$_3$ | CH$_3$ |
| 2* | CH$_3$ | CH$_3$ |
| 3* | CH$_3$ | CH$_3$ |
| 4 | Et | CH$_2$CH$_3$ |
| 5 | i-Bu | CH$_3$ |
| 6 | i-Bu | CF$_3$ |
| 7 | n-Bu | CH$_3$ |
| 8 | c-Hex | CH$_3$ |
| 9 | c-Hex | CF$_3$ |
| 10 | Phenyl | CH$_3$ |
| 11* | Phenyl | CH$_3$ |
| 12* | Phenyl | CH$_3$ |
| 13* | Phenyl | CH$_3$ |
| 14 | Phenyl | CF$_3$ |
| 15 | Phenyl | CH$_2$CH$_3$ |
| 16 | Phenyl | i-Pr |
| 17 | Phenyl | Phenyl |
| 18 | m-F-Phenyl | CH$_3$ |
| 19 | p-F-Phenyl | CH$_3$ |

TABLE 1-continued

Ib

| Example | R$^{1a}$ | R$^{1b}$ |
|---|---|---|
| 20 | p-Cl-Phenyl | CH$_3$ |
| 21* | p-Cl-Phenyl | CH$_3$ |
| 22* | p-Cl-Phenyl | CH$_3$ |
| 23* | p-Cl-Phenyl | CH$_3$ |
| 24* | p-Cl-Phenyl | CH$_3$ |
| 25 | o-CH$_3$-Phenyl | CF$_3$ |
| 26 | m-CH$_3$-Phenyl | CF$_3$ |
| 27 | p-CH$_3$-Phenyl | CF$_3$ |
| 28 | p-Et-Phenyl | CF$_3$ |
| 29 | p-MeSO$_2$-Phenyl | CH$_3$ |
| 30 | 2-Thiazolyl | CH$_3$ |
| 31 | 2-Thiazolyl | CF$_3$ |
| 35* | p-OH-phenyl | CH$_3$ |

Footnote:
All compounds are racemic mixtures unless indicated by *, in which case they are resolved or partially resolved stereoisomers.

Assays for Determining Biological Activity

Measurement of Whole-cell cAMP Content

CHO-K1 cells were plated at a density of $10^6$ cells/175 $cm^2$ containing complete media with 500 g/ml hygromycin. The flasks were maintained in an incubator at 37 C. with 5.0% $CO_2$ for 72 hr. The media was changed and the cells were allowed to grow overnight. The cells were washed and dissociated from the plate with PBS containing 0.5 mM EDTA. Cellular cAMP content was measured by centrifuging the cell suspension at 150 g×10 min. And resuspending the cells in a Hanks buffered salt solution at a density of $0.2×10^6$ cells/ml. The cells were preincubated at room temperature for 15 min. and then incubated with 10 M prostaglandin $I_2$ ($PGI_2$) and the indicated compound for an additional 10 min. Basal cAMP levels were determined by incubating the cells in 0.1% DMSO. The incubations were terminated by the addition of HCl (0.1 N final) and the cells measured for cAMP as described below.

Determinations of whole-cell cAMP content were performed by incubating 100 1 reconstituted rabbit anti-succinyl cAMP serum with 100 l of the whole-cell reaction or known cAMP standard and 30 pmol of $^{125}$I-cAMP TME in a ScintiStrip™ well (300 1 final volume) at room temperature for 8 h. Total cpm ($B_o$) was determined in the absence of sample of cAMP standard. The reaction mixture was then aspirated out of the well, and the individual wells were counted in a Beckman LS 6000SC with the window open from 10–999 for 1 min. The data were expressed as $\%B/B_o$=[(standard or sample cpm—non-specific cpm)/($B_o$ cpm—non-specific cpm)]×100. Non-specific cpm were determined by incubating only the $^{125}$I-cAMP TME with assay buffer (50 nM acetate; pH 5.8) in the ScintiStrip™ well. All determinations were performed in triplicate.

Phosphodiesterase Scintillation Proximity Assay

CHO-K1 cells were lysed by sonication for 10 secs at a power setting of 50% (Braunsonic Model 2000) in an ice cold solution containing 50 mM Tris, pH 7.5; 1 mM EDTA; and 200 M -mercaptoethanol. The soluble and particulate fractions of the cell were obtained by centrifuging the sonicate for 90 min. at 100,000×g at 4 C. PDE activity was measured in a solution containing 50 mM Tris, pH 7.5; 10 mM $MgCl_2$; 1 mM EDTA; and 100 nM (or indicated) $^3$H-cAMP (100 1 final volume) in the presence of varying concentrations of inhibitor. The reaction mixture containing enzyme was incubated for 10 min. at 30 C. in 96-well View Plates (Packard), and terminated by the addition of 50 1 Phosphodiesterase Scintillation Proximity Assay (SPA) Beads (Amersham) containing 18 mM $ZnSO_4$. The amount of $^3$H-cAMP hydrolysis was determined by counting the plates in a Wallac 1450 Beta LSC counter.

The Elevation of cAMP in Leukocytes

The effect of compounds of the invention on intracellular cAMP was investigated using human neutrophils or guinea pig eosinophils. Human neutrophils were separated from peripheral blood, incubated with dihydrocytochalasin B and the test compound for 10 min and then stimulated with FMLP. Guinea pig eosinophils were harvested by peritoneal lavage of animals previously treated with intra-peritoneal injections of human serum. Eosinophils were separated from the peritoneal exudate and incubated with isoprenaline and test compound. With both cell types, suspensions were centrifuged at the end of the incubation, the cell pellets were resuspended in buffer and boiled for 10 min prior to measurement of cAMP by specific radioimmunoassay (DuPont).

The most potent compounds according to the Examples induced a concentration-dependent elevation of cAMP in neutrophils and/or eosinophils at concentrations of 0.1 nM to 1 M.

Anti-allergic Activity in vivo

Compounds of the invention were tested for effects on an IgE-mediated allergic pulmonary inflammation induced by inhalation of antigen by sensitised guinea pigs. Guinea pigs were initially sensitised to ovalbumin under mild cyclophosphamide-induced immunosuppression, by intraperitoneal injection of antigen in combinations with aluminium hydroxide and pertussis vaccine. Booster doses of antigen were given two and four weeks later and at six weeks, animals were challenged with aerosolised ovalbumin whilst under cover of an intraperitoneally administered anti-histamine agent (mepyramine). After a further 48 h, bronchial alveolar lavages (BAL) were performed and the numbers of eosinophils and other leukocytes in the BAL fluids were counted. The lungs were also removed for histological examination for inflammatory damage. Administration of compounds of the Examples (0.001–10 mg/kg i.p. or p.o.), up to three times during the 48 h following antigen challenge, lead to a significant reduction in the eosinophilia and the accumulation of other inflammatory leukocytes. There was also less inflammatory damage in the lungs of animals treated with compounds of the Examples.

Adverse Effects

Compounds of the invention are substantially free from adverse effects following repeated overdosage to rats or dogs. For example, over administration of 125 mg/kg/day of active compounds of the Examples to rats for 30 days is not associated with adverse toxicity.

The most potent compounds of the invention are 20–30 times less active than rolipram in inducing behavioural changes, sedation or emesis in rats, ferrets or dogs.

SPA Based PDE Activity Assay Protocol

Compounds which inhibit the hydrolysis of cAMP to AMP by the type-IV cAMP-specific phosphodiesterases were screened in 96-well plate format as follows:

In a 96 well-plate at 30° C. was added the test compound (dissolved in 2 ul DMSO), 188 ml of substrate buffer containing [2,8-$^3$H] adenosine 3',5'-cyclic phosphate (cAMP, 100 nM to 50 $\mu$M), 10 mM $MgCl_2$, 1 mM EDTA, 50 mM Tris, pH 7.5. The reaction was initiated by the addition of 10 ml of human recombinant PDE-IV (the amount was controlled so that ~10% product was formed in 10 min. at 30° C.). The reaction was stopped after 10 min. by the addition of 1 mg of PDE-SPA beads (Amersham). The product AMP generated was quantified on a Microbeta 96-well plate counter. The signal in the absence of enzyme was defined as the background. 100% activity was defined as the signal detected in the presence of enzyme and DMSO with the background subtracted. Percentage of inhibition was calculated accordingly. $IC_{50}$ value was approximated with a non-linear regression fit of the standard 4-parameter/multiple binding sites equation from a ten point titration.

LPS and fMLP-Induced TNF-a and $LTB_4$ Assays in Human Whole Blood

Whole blood provides a protein and cell-rich milieu appropriate for the study of biochemical efficacy of anti-inflammatory compounds such as PDE IV-selective inhibitors. Normal non-stimulated human blood does not contain detectable levels of TNF- and $LTB_4$. Upon stimulation with LPS, activated monocytes expresss and secrete TNF- up to 8 hours and plasma levels remain stable for 24 hours. Published studies have shown that inhibition of TNF- by increasing intracellular cAMP via PDE IV inhibition and/or enhanced adenylyl cyclase activity occurs at the transcriptional level. $LTB_4$ synthesis is also sensitive to levels of intracellular cAMP and can be completely inhibited by PDE IV-selective inhibitors. As there is little $LTB_4$ produced during a 24 hour LPS stimulation of whole blood, an additional LPS stimulation followed by fMLP challenge of human whole blood is necessary for $LTB_4$ synthesis by activated neutrophils. Thus, using the same blood sample it is possible to evaluate the potency of a compound on two surrogate markers of PDE IV activity in the whole blood.

Fresh blood was collected in heparinized tubes by venipuncture from healthy human volunteers (male and female). These subjects had no apparent inflammatory conditions and had not taken any NSAIDs for at least 4 days prior to blood collection. Five hundred μL aliquots of blood were pre-incubated with either 2 μL of vehicle (DMSO) or 2 μL test compound at varying concentrations for 15 minutes at 37° C. This was followed by the addition of either 10 μL vehicle (PBS) as blanks or 10 μL LPS (1 μg/ml final concentration, Sigma Chem, #L-2630 from *E. coli*, serotype 0111:B4; diluted in 0.1% w/v BSA (in PBS)). After 24 hours of incubation at 37° C., another 10 μL of PBS (blank) or 10 μL of LPS (1 μg/ml final concentration) was added to blood and incubated for 30 minutes at 37° C. The blood was then challenged with either 10 μL of PBS (blank) or 10 μL of FMLP (1 μM final concentration, Sigma Chem #F-3506; diluted in 1% w/v BSA (in PBS)) for 15 minutes at 37° C. The blood samples were centrifuged at 1500×g for 10 minutes at 4° C. to obtain plasma. A 50 μL aliquot of plasma was mixed with 200 μL methanol for protein precipitation and centrifuged as above. The supernatant was assayed for $LTB_4$ using an enzyme immunoassay kit (Cayman Chemicals #520111) according to the manufacturer's procedure. TNF-a was assayed in diluted plasma (in PBS) using an ELISA kit (Cistron Biotechnology) according to manufacturer's procedure.

The invention is further illustrated by the following non-limiting examples in which, unless stated otherwise, operations were carried out at room or ambient temperature, that is, at a temperature in the range 18–25° C.; evaporation of solvent was carried out using a rotary evaporator under reduced pressure (600–4000 pascals: 4.5–30 mm. Hg) with a bath temperature of up to 60° C.; the course of reactions was followed by thin layer chromatography (TLC) and reaction times are given for illustration only; the structure and purity of all final products were assured by at least one of the following techniques: TLC, mass spectrometry, nuclear magnetic resonance (NMR) spectrometry or microanalytical data; yields are given for illustration only; when given, NMR data is in the form of delta ( ) values for major diagnostic protons, given in parts per million (ppm) relative to acetone-$d_5$ as internal standard, determined at 300 MHz, 400 MHz or 500 MHz using the indicated solvent; conventional abbreviations used for signal shape are: s. singlet; d. doublet; t. triplet; m. multiplet; br. broad; etc.; chemical symbols have their usual meanings; the following abbreviations have also been used: L (liter(s)), mL (milliliters), g (gram(s)), mg (milligrams(s)), mol (moles), mmol (millimoles), eq (equivalent(s)).

The following abbreviations have the indicated meanings:
Ac=Acetyl
Bn=benzyl
cAMP=cyclic adenosine-3',5'-monophosphate
DBU=1,8-diazabicyclo[5.4.0]undec-7-ene
DIBAL=diisobutylaluminum hydride
DMAP=4-(dimethylamino)pyridine
DMF=N,N-dimethylfonnamide
$Et_3N$=triethylamine
GST=glutathione transferase
LDA=lithium diisopropylamide
m-CPBA=metachloroperbenzoic acid
MMPP=monoperoxyphthalic acid
MPPM=monoperoxyphthalic acid, magnesium salt $6H_2O$
Ms=methanesulfonyl=mesyl=$SO_2Me$
MsO=methanesulfonate=mesylate
NSAID=non-steroidal anti-inflammatory drug
o-Tol=ortho-tolyl
OXONE®=$2KHSO_5.KHSO_4.K_2SO_4$
PCC=pyridinium chlorochromate
PDC=pyridinium dichromate
PDE phosphodiesterase
Ph=phenyl
Phe=benzenediyl
PMB=para-methoxybenzyl
Pye=pyridinediyl
r.t.=room temperature
rac.=racemic
SAM=aminosulfonyl or sulfonamide or $SO_2NH_2$
SEM=2-(trimethylsilyl)ethoxymethoxy
SPA=scintillation proximity assay
TBAF=tetra-n-butylammonium fluoride
Th=2- or 3-thienyl
TFA=trifluoroacetic acid
TFAA=trifluoroacetic acid anhydride
THF=tetrahydrofuran
Thi=thiophenediyl
TLC=thin layer chromatography
TMS-$CF_3$=trimethyl(trifluoromethyl)silane
TMS-CN=trimethylsilyl cyanide
Tz=1H (or 2H)-tetrazol-5-yl
$C_3H_5$=allyl Alkyl Group Abbreviations Me=methyl
Et=ethyl
n-Pr=normal propyl
i-Pr=isopropyl
n-Bu=normal butyl
i-Bu=isobutyl
s-Bu=secondary butyl
t-Bu=tertiary butyl
c-Pr=cyclopropyl
c-Bu=cyclobutyl
c-Pen=cyclopentyl
c-Hex=cyclohexyl

Preparation of Intermediates

INTERMEDIATE 1
(±)-4-{2-[3,4-BIS(DIFLUOROMETHOXY)[PHENYL]-2-[5-(2-FORMYL)PYRIDYL]ETHYL}PYRIDINE

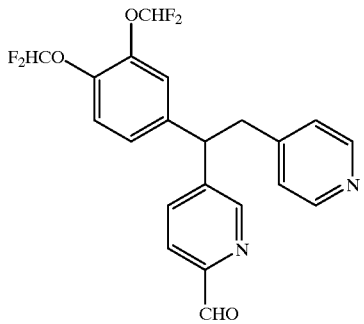

Step 1: (±)-3,4-Bis(difluoromethoxy)phenyl-5-(2-bromo)pyridylcarbinol

To a solution of 2,5-dibromopyridine (56.9 g, 240 mmol) in anhydrous ether at −73° C. was added n-BuLi (200 mL of a 1.2 M solution in hexane, 240 mmol) over 15 min. After 15 min, 3,4-bis(difluoromethoxy)benzaldehyde (47.6 g, 200 mmol) in anhydrous ether (300 mL) was added via cannula over 20 min. The mixture was stirred at −73° C. for 20 min and then the temperature was slowly raised to −40° C. over 40 min. The mixture was poured into water (1 L) and 1 N HCl (300 mL) and extracted with ether. The organic layer was washed with brine, dried (MgSO$_4$) and concentrated. Flash chromatography of the residue (silica gel; ethyl acetate/hexane 20:80 to 40:60) provided the title product as a reddish oil (42.2 g).

Step 2: (±)-4-{2-[3,4-Bis(difluoromethoxy)phenyl]-2-[5-(2-bromo)pyridyl]ethyl}pyridine

To a solution of (±)-3,4-bis(difluoromethoxy)phenyl-5-(2-bromo)pyridylcarbinol from Step 1 (28.9 g, 73 mmol) in dichloromethane (340 mL) at 25° C. was added thionyl chloride (6.92 mL, 94.8 mmol) and the resulting mixture was stirred at this temperature for 45 min. The mixture was carefully poured into sat. NaHCO$_3$ (700 mL), the phases were separated and the aqueous phase extracted with dichloromethane. The combined organics were washed with sat. NaHCO$_3$, brine, dried (MgSO$_4$) and concentrated to provide the crude chloride as a yellow oil (28.7 g) that was used immediately.

To a solution of ethyl 4-pyridylacetate (31.8 mL, 208 mmol) in THF (830 mL) and HMPA (36.1 mL, 208 mmol) at 25° C. was added potassium bis(trimethylsilyl)amide (415 mL of a 0.5 M solution in toluene, 208 mmol). The resulting mixture was stirred for 20 min and then a THF (175 mL) solution of the chloride prepared above was added over 15 min and then stirred for 15 h at 25° C. The mixture was poured into sat. NH$_4$Cl (1.5 L) and extracted twice with ethyl acetate. The combined organics were washed successively with 25% NH$_4$OAc buffer, brine, dried (MgSO$_4$) and concetrated to give a thick orange-brown oil. This material was dissolved in a mixture of THF/MeOH/water (3:1:1, 1 L), 2N LiOH (312 mL, 623 mmol) was added and the mixture was heated at 70° C. for 2 h. After cooling to 25° C., 2N HCl (333 mL) was slowly added, bringing the pH to approximately 4, and the mixture was stirred for 1 h. The volatiles were removed on the rotovap and the residue was partitioned between sat. NaHCO$_3$ and ethyl acetate. The aqueous phase was extracted twice with ethyl acetate and the combined organics were washed successively with 25% NH$_4$OAc buffer, water (3X), brine, dried (MgSO$_4$) and concetrated to give a brown gum. Flash chromatography (silica gel; ethyl acetate/hexane 3:2 to 100% ethyl acetate) provided the title product as a yellow gum (31.2 g).

Step 3: (±)-4-{2-[3,4-Bis(difluoromethoxy)phenyl]-2-[5-(2-vinyl)pyridyl]ethyl}pyridine

A solution of (±)-4-{2-[3,4-bis(difluoromethoxy)phenyl]-2-[5-(2-bromo)pyridyl]ethyl}pyridine from Step 2 (4.87 g, 10 mmol) in dioxane (60 mL) was degassed with Ar and then bis(triphenylphosphine)palladium dichloride (351 mg, 0.5 mmol) and tributyl(vinyl)stannane (4.4 mL, 15 mmol) were added. The mixture was heated at reflux for 15 h and then additional bis(triphenylphosphine)palladium dichloride (200 mg) and tributyl(vinyl)stannane (2 mL) were added. After an additional 4h at reflux, the mixture was cooled to 25° C. and 25% NH$_4$OAc buffer was added. The mixture was extracted thrice with ethyl acetate and the combined organics were washed with brine, dried (MgSO$_4$) and concetrated. Flash chromatography (silica gel; ethyl acetate/hexane 70:30 to 100% ethyl acetate followed by ethanol/ethyl acetate 5:95 to 1:9) provided the title product as a light orange oil (3.84 g).

Step 4: (±)-4-{2-[3,4-Bis(difluoromethoxy)phenyl]-2-[5-(2-formyl)pyridyl]ethyl}pyridine

Ozone was bubbled through a solution of (±)-4-{2-[3,4-bis(difluoromethoxy)phenyl]-2-[5-(2-vinyl)pyridyl]ethyl}pyridine from Step 3 (3.8 g, 9.1 mmol) in ethyl acetate (50 mL) at −78° C. for 15 min during which time the solution changed color from yellow to orange. The solution was purged with nitrogen and then dimethyl sulfide (3.3 mL, 45.5 mmol) was added. The cooling bath was removed, the mixture was stirred at 25° C. for 80 min and was then concentrated in vacuo. Dichloromethane was added to the residue and the soluble material was decanted off and concentrated. Flash chromatography of the residue (silica gel; ethyl acetate) provided the title product as a yellow oil (2.26 g). $^1$H NMR (400 MHz, acetone-d$_6$): 3.59 (d, 2H), 4.79 (t, 1H), 6.94 (t, 1H), 6.95 (t, 1H), 7.21 (m, 2H), 7.29 (d, 1H), 7.39 (dd, 1H), 7.47 (dd, 1H), 7.84 (dd, 1H), 8.06 (dd, 1H), 8.37 (m, 2H), 8.80 (d, 1H), 9.92 (s, 1H).

INTERMEDIATE 2
(±)-4-{2-[3,4-BIS(DIFLUOROMETHOXY)PHENYL]-2-[5-(2-N-METHOXY-N-METHYLFORMAMIDYL)PYRIDYL]ETHYL}PYRIDINE

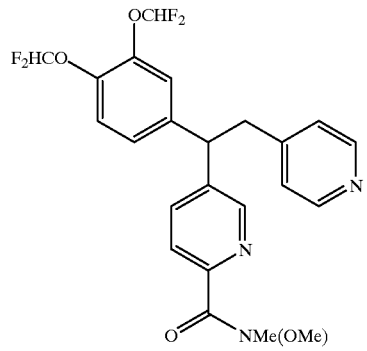

Step 1: (±)-4-{2-[3,4-Bis(difluoromethoxy)phenyl]-2-[5-(2-carbomethoxy)pyridyl]ethyl}pyridine

To a solution of (±)-4-{2-[3,4-bis(difluoromethoxy)phenyl]-2-[5-(2-bromo)pyridyl]ethyl}pyridine from Intermediate 1, Step 2 (16.4 g, 34.8 mmol) in DMF (33 mL) was successively added palladium(II) acetate (469 mg, 2.1 mmol), dppf (2.32 g, 4.2. mmol), triethylamine (9.7 mL, 69.6 mmol) and MeOH (33 mL). The mixture was cooled to 0° C. and degassed by bubbling Ar through the mixture for 10 min and then evacuated under reduced pressure. The mixture was then placed under an atmosphere of CO (1 atm, balloon) and heated at 50° C. for 20 h. The mixture was cooled to 25° C. and the volatiles were removed in vacuo. The residue was partitioned between water (300 mL) and ethyl acetate and the aqueous phase was extracted thrice with ethyl acetate. The combined organics were washed three times with water, dried (MgSO$_4$) and concetrated. Flash chromatography of the residue (silica gel; acetone/toluene 2:3 to 3:2) provided the title product as an orange-brown gum (14.7 g) that was contaminated by dppf by-products, and was used as such in the next step.

Step 2: (±)-4-{2-[3,4-Bis(difluoromethoxy)phenyl]-2-[5-(2-N-methoxy-N-methylformamidyl)pyridyl]ethyl}pyridine To a THF (500 mL) solution of methoxymethylamine (7 mL, 100 mmol) at −78° C. was slowly added, over 10 min, MeMgBr (33.3 mL of a 3M solution in ether). The mixture was stirred at −78° C. for 30 min and then a solution of (±)-4-{2-[3,4-bis(difluoromethoxy)phenyl]-2-[5-(2-carbomethoxy)pyridyl]ethyl}pyridine from Step 1 (15 g) in THF (300 mL) was added over 5 min via cannula. The resulting mixture was slowly warmed to 0° C. over 2.5 h and then the mixture was poured into 25% NH4OAc buffer (1 L) and extracted four times with ethyl acetate. The combined organics were washed with water, brine, dried (MgSO$_4$) and concetrated. Flash chromatography of the residue (silica gel; ethanol/chloroform 3:97 to 5:95) provided the title product as an orange-brown gum (14.4 g).

$^1$H NMR (500 MHz, acetone-d$_6$): 3.23 (br s, 3H), 3.56 (m, 2H), 3.69 (s, 3H), 4.69 (t, 1H), 6.93 (t, 1H), 6.95 (t, 1H), 7.19 (m, 2H), 7.28 (d, 1H), 7.37 (dd, 1H), 7.44 (d, 1H), 7.53 (br s, 1H), 7.93 (dd, 1H), 8.36 (m, 2H), 8.57 (d, 1H).

EXAMPLES

All examples are mixtures of stereoisomers, either racemic mixtures (indicated as (±)) or racemic mixtures of diastereomers (indicated as (±/±)) unless stated otherwise. In those cases in which the stereoisomers have been separated, they are so indicated by Enantiomer 1, 2 etc. or Diastereomer 1, 2 etc.

Example 1

(±)-4-{2-[3,4-BIS(DIFLUOROMETHOXY)PHENYL]-2-{5-[2-(1-HYDROXY-1-METHYL)ETHYL]PYRIDYL}ETHYL}PYRIDINE N-OXIDE

Step 1: (±)-4-{2-[3,4-Bis(difluoromethoxy)phenyl]-2-[5-(2-carbomethoxy)pyridyl]ethyl}pyridine N-oxide To a solution of (±)-4-{2-[3,4-bis(difluoromethoxy)phenyl]-2-[5-(2-carbomethoxy)pyridyl]ethyl}pyridine from Intermediate 2, Step 1 (2.17 g, 4.82 mmol) in dichloromethane/methanol (40 mL, 9:1) at 25° C. was added MMPP (4.77 g, 9.64 mmol) and the mixture was stirred for 22 h. The mixture was diluted with ethyl acetate and washed successively with sat. NaHCO$_3$, brine, dried (MgSO$_4$) and concentrated. Flash chromatography of the residue (silica gel, chloroform/ethanol 9:1) provided the title compound as a white foam (1.74 g).

Step 2: (±)-4-{2-[3,4-Bis(difluoromethoxy)phenyl]-2-{5-[2-(1-hydroxy-1-methyl)ethyl]pyridyl}ethyl}pyridine N-oxide To a solution of (±)-4-{2-[3,4-bis(difluoromethoxy)phenyl]-2-[5-(2-carbomethoxy)pyridyl]ethyl}pyridine N-oxide from Step 1 (253 mg, 0.54 mmol) in dichloromethane (6 mL) at −78° C. was added MeMgCl (0.54 mL of a 3M solution in THF, 1.62 mmol). After 2.5 h, an additional amount of MeMgCl (0.6 mL of a 3M solution in THF) was added and the mixture stirred for 3.5 h. 25% NH$_4$OAc buffer was added at −78° C., the mixture was extracted with ethyl acetate, and the organics were washed with brine, dried (MgSO$_4$) and concentrated. Flash chromatography of the residue (silica gel, chloroform/ethanol 9:1) provided the title compound as a white foam (123 mg).

$^1$H NMR (500 MHz, acetone-d$_6$): 1.43 (s, 6H), 3.51 (m, 2H). 4.58 (t, 1H), 4.61 (br s, 1H), 6.93 (t, 1H), 6.96 (t, 1H), 7.20 (d, 2H), 7.27 (d, 1H), 7.35 (dd, 1H), 7.42 (s, 1H), 7.58 (d, 1H), 7.82 (dd, 1H), 7.94 (d, 2H), 8.49 (s, 1H).

Examples 2 and 3

ENANTIOMERS OF 4-{2-[3,4-BIS(DIFLUOROMETHOXY)PHENYL]-2-{5-[2-(1-HYDROXY-1-METHYL)ETHYL]PYRIDYL}ETHYL}PYRIDINE N-OXIDE

A solution of (±)-4-{2-[3,4-bis(difluoromethoxy)phenyl]-2-{5-[2-(1-hydroxy-1-methyl)ethyl]pyridyl}ethyl}pyridine N-oxide (Example 1; 1.26 g) in ethanol/hexane (4 mL, 1:1) was injected onto a chiralpack AD preparative HPLC column (eluting with hexane/ethanol 4:1 at 60 mL/min with UV detection at 300 nm). The enantiomers were separated with the faster eluting enantiomer having a retention time of ~21 min (Enantiomer 1, Example 2) and the slower eluting enantiomer (Enantiomer 2, Example 3) having a retention time of ~24 min. The eluants were concentrated to provide the title compounds as white foams: Enantiomer 1 (458 mg) and Enantiomer 2 (173 mg).

Example 4

(±)-4-{2-[3,4-BIS(DIFLUOROMETHOXY)PHENYL]-2-{5-[2-(1-ETHYL-1-HYDROXY)PROPYL]PYRIDYL}ETHYL}PYRIDINE N-OXIDE

Step 1: (±)-4-{2-[3,4-Bis(difluoromethoxy)phenyl]-2-{5-[2-(1-ethyl-1-hydroxy)propyl]pyridyl}ethyl}pyridine To a mixture of (±)-4-{2-[3,4-bis(difluoromethoxy)phenyl]-2-[5-(2-carbomethoxy)pyridyl]ethyl}pyridine from Intermediate 2, Step 1 (329 mg, 0.73 mmol) and LiCl (247 mg) in ether (6 mL) at 25° C. was added EtMgCl (1.18 mL of a 2M solution in ether) and the resulting mixture was heated at reflux for 45 min and then stirred at 25° C. for 2.5 h. The reaction was quenched by the addition of 25% NH$_4$OAc buffer, extracted with ethyl acetate and the organics were washed with brine, dried (MgSO$_4$), and concentrated. The residue was a mixture of the title compound and the corresponding ketone (3.3:1). The mixture was dissolved in dichloromethane (4 mL) and treated at −78° C. with EtMgCl (0.4 mL of a 2M solution in ether). After 2.75 h, 25% NH$_4$OAc buffer was added and the mixture was extracted with ethyl acetate. The organics were washed with brine, dried (MgSO$_4$), and concentrated. Flash chromatography of the residue (silica gel, ethyl acetate) provided the title compound as an amber gum (195 mg).

Step 2: (±)-4-{2-[3,4-Bis(difluoromethoxy)phenyl]-2-{5-[2-(1-ethyl-1-hydroxy)propyl]pyridyl}ethyl}pyridine N-oxide Following the procedures described in Example 1, Step 1, but substituting (±)-4-{2-[3,4-bis(difluoromethoxy)phenyl]-2-{5-[2-(1-ethyl-1-hydroxy)propyl]pyridyl}ethyl}pyridine from Step 1 (195 mg) for (±)-4-{2-[3,4-bis(difluoromethoxy)phenyl]-2-[5-(2-carbomethoxy)pyridyl]ethyl}pyridine, and eluting with ethyl acetate/ethanol (4:1) during flash chromatography, the title compound was obtained as a white foam (68 mg).

$^1$H NMR (400 MHz, acetone-d$_6$): 0.57 (t, 6H), 1.70–1.85 (m, 4H), 3.50 (m, 2H), 4.55 (t, 1H), 4.67 (s, 1H), 6.93 (t, 1H), 6.96 (t, 1H), 7.15 (d, 2H), 7.27 (d, 1H), 7.34 (d, 1H), 7.41 (s, 1H), 7.47 (d, 1H), 7.81 (d, 1H), 7.93 (d, 2H), 7.27 (d, 1H), 7.34 (d, 1H), 7.47 (d, 1H), 7.81 (d, 1H), 7.93 (d, 2H), 8.48 (s, 1H).

Example 5

(±/±)-4-{2-[3,4-BIS(DIFLUOROMETHOXY)PHENYL]-2-{5-[2-(1-HYDROXY-1-ISOBUTYL)ETHYL]PYRIDYL}ETHYL}PYRIDINE N-OXIDE

Step 1: (±)-4-{2-[3,4-Bis(difluoromethoxy)phenyl]-2-{5-[2-(1-keto-3-methyl)butyl]pyridyl}ethyl}pyridine To a solution of Intermediate 2 (633 mg, 1.32 mmol) in THF (15 mL) at −78° C. was added i-BuMgBr (2 mL of a 2 M solution in ether). The mixture was stirred at −78° C. for 2 h and then at 0° C. for 1.5 h. 25% NH$_4$OAc buffer was added and the mixture was extracted with ethyl acetate. The organics were washed with brine, dried (MgSO$_4$), and concentrated. Flash chromatography of the residue (silica gel, ethyl acetate/hexane 3:1) provided the title compound as a yellow gum (207 mg).

Step 2: (±)-4-{2-[3,4-Bis(difluoromethoxy)phenyl]-2-{5-[2-(1-keto-3-methyl)butyl]pyridyl}ethyl}pyridine N-oxide Following the procedures described in Example 1, Step 1, but substituting (±)-4-{2-[3,4-bis(difluoromethoxy)phenyl]-2-{5-[2-(1-keto-3-methyl)butyl]pyridyl}ethyl}pyridine from Step 1 (207 mg) for (±)-4-{2-[3,4-bis(difluoromethoxy)phenyl]-2-[5-(2-carbomethoxy)pyridyl]ethyl}pyridine, and eluting with ethyl acetate/ethanol (4:1) during flash chromatography, the title compound was obtained as a colorless gum (189 mg).

Step 3: (±/±)-4-{2-[3,4-Bis(difluoromethoxy)phenyl]-2-{5-[2-(1-hydroxy-1-isobutyl)ethyl]pyridyl}ethyl}pyridine N-oxide To a solution of (±)-4-{2-[3,4-bis(difluoromethoxy)phenyl]-2-{5-[2-(1-keto-3-methyl)butyl]pyridyl}ethyl}pyridine N-oxide from Step 2 (81.4 mg, 0.17 mmol) in dichloromethane (2.5 mL) at −78° C. was added MeMgCl (0.28 mL of a 3M solution in THF). The mixture was stirred at −78° C. for 3 h and then 25% NH$_4$OAc buffer was added and the mixture was extracted with ethyl acetate. The organics were washed with brine, dried (MgSO$_4$), and concentrated. Flash chromatography of the residue (silica gel, ethyl acetate/ethanol 9:1) provided the title compound as a yellow gum (67 mg).

$^1$H NMR (400 MHz, acetone-d$_6$): 0.50 (dd, 3H), 0.83 (d, 3H), 1.41 (s, 3H), 1.53 (m, 1H), 1.66 (m, 1H), 1.75 (m, 1H), 3.50 (m, 2H), 4.56 (t, 1H), 6.93 (t, 1H), 6.96 (t, 1H), 7.17 (d, 2H), 7.28 (d, 1H), 7.35 (d, 1H), 7.42 (s, 1H), 7.55 (m, 1H), 7.80 (m, 1H), 7.92 (d, 2H), 8.47 (s, 1H).

Example 6

(±/±)-4-{2-[3,4-BIS(DIFLUOROMETHOXY)PHENYL]-2-{5-[2-(1-HYDROXY-1-ISOBUTYL)TRIFLUOROETHYL]PYRIDYL}ETHYL}PYRIDINE N-OXIDE

To a solution of (±)-4-{2-[3,4-bis(difluoromethoxy)phenyl]-2-{5-[2-(1-keto-3-methyl)butyl]pyridyl}ethyl}pyridine N-oxide from Example 5, Step 2 (88.6 mg, 0.18 mmol) in THF (2 mL) at 0° C. was added TMS-CF$_3$ (0.08 mL, 0.54 mmol) followed by TBAF (18 mL of a 1M solution in THF). The mixture was stirred at 25° C. for 5 h and then 1N HCl (1.5 mL) was added and the mixture was extracted with ethyl acetate. The organics were washed with brine, dried (MgSO$_4$), and concentrated. Flash chromatography of the residue (silica gel, dichloromethane/methanol 95:5) provided the title compound as a colorless gum (52 mg).

$^1$H NMR (400 MHz, acetone-d$_6$): 0.50 (d, 3H), 0.86 (d, 3H), 1.49 (m, 1H), 1.95 (m, 1H), 2.14 (m, 1H), 3.55 (m, 2H), 4.68 (t, 1H), 6.12 (s, 1H), 6.94 (t, 1H), 6.96 (t, 1H), 7.19 (d, 2H), 7.29 (d, 1H), 7.37 (m, 1H), 7.45 (m, 1H), 7.59 (d, 1H), 7.96 (d, 2H), 8.01 (dd, 1H), 8.62 (dd, 1H).

Example 7

(±/±)-4-{2-[3,4-BIS(DIFLUOROMETHOXY)PHENYL]-2-{5-[2-(1-HYDROXY-1-METHYL)PENTYL]PYRIDYL}ETHYL}PYRIDINE N-OXIDE

Step 1: (±)-4-{2-[3,4-Bis(difluoromethoxy)phenyl]-2-{5-[2-(1-keto)pentyl]pyridyl}ethyl}pyridine To a solution of Intermediate 2 (268 mg, 0.56 mmol) in THF (2.5 mL) at −78° C. was added n-BuLi (0.24 mL of a 2.4 M solution in hexane). The mixture was stirred at −78° C. for 45 min after which an additional portion of n-BuLi (0.24 mL) was added. After 30 min, 25% NH$_4$OAc buffer was added and the mixture was extracted with ethyl acetate. The organics were washed with brine, dried (MgSO$_4$), and concentrated. Flash chromatography of the residue (silica gel, ethyl acetatelhexane 7:3) provided the title compound as a pale yellow gum (135 mg).

Step 2: (±)-4-{2-[3,4-Bis(difluoromethoxy)phenyl]-2-{5-[2-(1-keto)pentyl]pyridyl}ethyl}pyridine N-oxide Following the procedures described in Example 1, Step 1, but substituting (±)-4-{2-[3,4-bis(difluoromethoxy)phenyl]-2-{5-[2-(1-keto)pentyl]pyridyl}ethyl}pyridine from Step 1 (125 mg) for (±)-4-{2-[3,4-bis(difluoromethoxy)phenyl]-2-[5-(2-carbomethoxy)pyridyl]ethyl}pyridine, and eluting with chloroform/ethanol (9:1) during flash chromatography, the title compound was obtained as a colorless gum (105 mg).

Step 3: (±/±)-4-{2-[3,4-Bis(difluoromethoxy)phenyl]-2-{5-[2-(1-hydroxy-1-methyl)pentyl]pyridyl}ethyl}pyridine N-oxide Following the procedures described in Example 5, Step 3, but substituting (±)-4-{2-[3,4-bis(difluoromethoxy)phenyl]-

2-{5-[2-(1-keto)pentyl]pyridyl}ethyl}pyridine N-oxide from Step 2 (103 mg) for (±)-4-{2-[3,4-bis(difluoromethoxy)phenyl]-2-{5-[2-(1-keto-3-methyl)butyl]pyridyl}ethyl}pyridine N-oxide, and eluting with chloroform/ethanol (9:1) during flash chromatography, the title compound was obtained as a white foam (64 mg).

$^1$H NMR (400 MHz, acetone-$d_6$): 0.78 (t, 3H), 0.80–0.91 (m, 1H), 1.10–1.34 (m, 3H), 1.41 (s, 3H), 1.66–1.83 (m, 2H), 3.50 (m, 2H), 4.56 (t, 1H), 6.93 (t, 1H), 6.96 (t, 1H), 7.18 (d, 2H), 7.27 (d, 1H), 7.35 (d, 1H), 7.41 (s, 1H), 7.53 (d, 1H), 7.81 (d, 1H), 7.92 (d, 2H), 8.48 (s, 1H).

Example 8

(±/±)-4-{2-[3,4-BIS(DIFLUOROMETHOXY)PHENYL]-2-{5-[2-(1-CYCLOHEXYL-1-HYDROXY)ETHYL]PYRIDYL}ETHYL}PYRIDINE N-OXIDE

Step 1: (±)-4-{2-[3,4-Bis(difluoromethoxy)phenyl]-2-{5-[2-(1-keto)cyclohexylmethyl]pyridyl}ethyl}pyridine Following the procedures described in Example 5, Step 1, but substituting cyclohexylmagnesium chloride for i-BuMgBr, and eluting with ethyl acetate/ethanol (95:5) during flash chromatography, the title compound was obtained as a yellow gum (452 mg).

Step 2: (±)-4-{2-[3,4-Bis(difluoromethoxy)phenyl]-2-{5-[2-(1-keto)cyclohexylmethyl]pyridyl}ethyl}pyridine N-oxide Following the procedures described in Example 1, Step 1, but substituting (±)-4-{2-[3,4-bis(difluoromethoxy)phenyl]-2-{5-[2-(1-keto)cyclohexylmethyl]pyridyl}ethyl}pyridine from Step 1 (288 mg) for (±)-4-{2-[3,4-bis(difluoromethoxy)phenyl]-2-[5-(2-carbomethoxy)pyridyl]ethyl}pyridine, and eluting with ethyl acetate/ethanol (4:1) during flash chromatography, the title compound was obtained as a white foam (79 mg).

Step 3: (±/±)4-{2-[3,4-Bis(difluoromethoxy)phenyl]-2-{5-[2-(1-cyclohexyl-1-hydroxy)ethyl]pyridyl}ethyl}pyridine N-oxide Following the procedures described in Example 5, Step 3, but substituting (±)-4-{2-[3,4-bis(difluoromethoxy)phenyl]-2-{5-[2-(1-keto)cyclohexylmethyl]pyridyl}ethyl}pyridine N-oxide from Step 2 (79 mg) for (±)-4-{2-[3,4-bis(difluoromethoxy)phenyl]-2-{5-[2-(1-keto-3-methyl)butyl]pyridyl}ethyl}pyridine N-oxide, and eluting with chloroform/ethanol (9:1) during flash chromatography, the title compound was obtained as a white foam (49 mg).

$^1$H NMR (500 MHz, acetone-$d_6$): 0.95–1.30 (m, 6H), 1.39 (s, 3H), 1.55–1.83 (m, 5H), 3.50 (m, 2H), 4.56 (t, 1H), 6.93 (t, 1H), 6.95 (t,1H), 7.16 (d, 2H), 7.28 (d, 1H), 7.35 (d, 1H), 7.41 (s, 1H), 7.57 (d, 1H), 7.80 (m, 1H), 7.92 (d, 2H), 8.48 (s, 1H).

Example 9

(±/±)-4-{2-[3,4-BIS(DIFLUOROMETHOXY)PHENYL]-2-{5-[2-(1-CYCLOHEXYL-1-HYDROXY)TRIFLUOROETHYL]PYRIDYL}ETHYL}PYRIDINE N-OXIDE

Following the procedures described in Example 6, but substituting (±)-4-{2-[3,4-bis(difluoromethoxy)phenyl]-2-{5-[2-(1-keto)cyclohexylmethyl]pyridyl}ethyl}pyridine N-oxide from Example 8, Step 2 (38 mg) for (±)-4-{2-[3,4-bis(difluoromethoxy)phenyl]-2-{5-[2-(1-keto-3-methyl)butyl]pyridyl}ethyl}pyridine N-oxide, and eluting with dichloromethane/ethanol (95:5) during flash chromatography, the title compound was obtained as a yellow gum (11 mg).

$^1$H NMR (400 MHz, acetone-$d_6$): 1.00–1.15 (m, 3H), 1.20–1.45 (m, 3H), 1.57 (m, 2H), 1,78 (m, 1H), 1.96 (m, 1H), 2.20 (m, 1H), 3.54 (m, 2H), 4.65 (t, 1H), 6.94 (t, 1H), 6.95 (t, 1H), 7.18 (m, 2H), 7.29 (d, 1H), 7.38 (d, 1H), 7.44 (s, 1H), 7.63 (d, 1H), 7.93 (d, 2H), 7.99 (m, 1H), 8.60 (m, 1H).

Example 10

(±/±)-4-{2-[3,4-BIS(DIFLUOROMETHOXY)PHENYL]-2-{5-[2-(1-HYDROXY-1-PHENYL)ETHYL]PYRIDYL}ETHYL}PYRIDINE N-OXIDE

Step 1: (±)-4-{2-[3,4-Bis(difluoromethoxy)phenyl]-2-[5-(2-benzoyl)pyridyl]ethyl}pyridine To a solution of Intermediate 1 (5 g, 11.9 mmol) in dichloromethane (100 mL) at −78° C. was added PhMgCl (8 mL of a 2M solution in THF, 16 mmol) dropwise. After 2 h, the mixture was partitioned between sat. NH$_4$Cl and ethyl acetate. The organic layer was washed with brine, dried (MgSO$_4$) and concentrated. The residue was dissolved in dichloromethane (100 mL), manganese(IV) oxide (8 g) was added and the mixture was heated at reflux 24 h. An additional portion of manganese(IV) oxide (8 g) was added and the mixture was stirred at 25° C. for 4 h. The mixture was filtered through a pad of Celite, washing with dichloromethane, and the filtrate was concentrated. Flash chromatography of the residue (silica gel; ethyl acetate/hexane 4:1) provided the title compound as a colorless oil (2.2 g).

Step 2: (±/±)-4-{2-[3,4-Bis(difluoromethoxy)phenyl]-2-{5-[2-(1-hydroxy-1-phenyl)ethyl]pyridyl}ethyl}pyridine To a solution of (±)-4-{2-[3,4-bis(difluoromethoxy)phenyl]-2-[5-(2-benzoyl)pyridyl]ethyl}pyridine from Step 1 (220 mg, 0.47 mmol) in dichloromethane (5 mL) at −78° C. was added MeMgCl (0.3 mL of a 3M solution in THF). The mixture was stirred at −78° C. for 2 h and then sat. NH$_4$Cl was added and the mixture was extracted with ether. The organics were washed with brine, dried (MgSO$_4$), and concentrated. Flash chromatography of the residue (silica gel, chloroform/methanol 95:5) provided the title compound as an oil (150 mg).

Step 3: (±/±)-4-{2-[3,4-Bis(difluoromethoxy)phenyl]-2-{5-[2-(1-hydroxy-1-phenyl)ethyl]pyridyl}ethyl}pyridine N-oxide A mixture of (±/±)-4-{2-[3,4-bis(difluoromethoxy)phenyl]-2-{5-[2-(1-hydroxy-1-phenyl)ethyl]pyridyl}ethyl}pyridine from Step 2 (150 mg, 0.3 mmol) and 80% mCPBA (75 mg) in chloroform (6 mL) was stirred at −20° C. for 5 min and then at 10° C. for 2 h. Solid calcium hydroxide was added and after 15 min, the mixture was filtered. The filtrate was concentrated and flash chromatography of the residue (silica gel; chloroform/methanol 98:2 to 95:5) provided the title compound as a white foam (50 mg).

$^1$H NMR (500 MHz, acetone-$d_6$): 1.87 (s, 3H), 3.50 (m, 2H), 4.59 (t, 1H), 5.35 (br s, 1H), 6.90 (t, 1H), 6.92 (t, 1H), 7.13–7.16 (m, 3H), 7.23–7.26 (m, 3H), 7.33 (d, 1H), 7.39 (s, 1H), 7.50–7.54 (m, 3H), 7.78 (m, 1H), 7.92 (m, 2H), 8.48 (m, 1H).

Examples 11–13

DIASTEREOMERS OF 4-{2-[3,4-BIS (DIFLUOROMETHOXY)PHENYL]-2-{5-[2-(1-HYDROXY-1-PHENYL)ETHYL] PYRIDYL}ETHYL}PYRIDINE N-OXIDE

Step 1: (±)-4-{2-[3,4-Bis(difluoromethoxy)phenyl]-2-[5-(2-benzoyl)pyridyl]ethyl}pyridine N-oxide To a solution of (±)-4-{2-[3,4-bis(difluoromethoxy) phenyl]-2-[5-(2-benzoyl)pyridyl]ethyl}pyridine from Example 10, Step 1 (6.1 g, 12.3 mmol) in dichloromethane/methanol (132 mL, 10:1) AT 25° C. was added MMPP (6.1 g, 12.3 mmol). After stirring for 3.5 h, an additional portion of MMPP (1 g) was added. After 1.5 h, the mixture was poured into sat. NaHCO$_3$ (500 mL) and the mixture was extracted with dichloromethane three times. The combined organics were washed with water, dried (MgSO$_4$) and concentrated. Flash chromatography of the residue (silica gel; dichloromethane/ethanol 95:5 to 9:1) provided the title compound as a white foam (5.3 g).

Step 2: Separation of Enantiomers of 4-{2-[3,4-bis (difluoromethoxy)phenyl]-2-[5-(2-benzoyl)pyridyl] ethyl}pyridine N-oxide (±)-4-{2-[3,4-Bis(difluoromethoxy)phenyl]-2-[5-(2-benzoyl)pyridyl]ethyl}pyridine N-oxide from Step 1 (6.3 g) was dissolved in isopropanol/hexane (1:1, 100 mg/mL). The enantiomers were separated by injection of 8 mL aliquots onto a Chiral Pak AD preparative HPLC column (5×50 cm) (eluting with hexane/isopropanol 3:1 at 70 mL/min with UV detection at 310 nm). The enantiomers were separated with the faster eluting enantiomer having a retention time of ~44 min (Enantiomer 1) and the slower eluting enantiomer (Enantiomer 2) having a retention time of ~54 min. The eluants were concentrated to provide the title compounds as white foams: Enantiomer 1 (3 g) and Enantiomer 2 (3 g).

Step 3: Mixture of Diastereomers 1 and 2 of 4-{2-[3,4-Bis(difluoromethoxy)phenyl]-2-{5-[2-(1-hydroxy-1-phenyl)ethyl]pyridyl}ethyl}pyridine N-oxide To a solution of Enantiomer 1 from Step 2 (3.0 g, 5.9 mmol) in dichloromethane (140 mL) at −78° C. was added three portions of MeMgBr (7.9 mL of a 3M solution in ether) over 1.75 h. 25% NH$_4$OAc buffer (500 mL) was added and the mixture was extracted with dichloromethane. The organics were washed successively with water, brine, dried (MgSO$_4$), and concentrated. Flash chromatography of the residue (silica gel, dichloromethane/ethanol 95:5 to 85:15) provided the title compound as a white foam (2.12 g).

Step 4: Separation of Diastereomers 1 and 2 of 4-{2-[3,4-Bis(difluoromethoxy)phenyl]2-{5-[2-(1-hydroxy-1-phenyl)ethyl]pyridyl}ethyl}pyridine N-oxide The mixture of 4-{2-[3,4-bis(difluoromethoxy)phenyl]-2-{5-[2-(1-hydroxy-1-phenyl)ethyl]pyridyl}ethyl}pyridine N-oxide diastereomers from Step 3 (2.5 g) was dissolved in ethanol/hexane (1:2, 100 mg/mL). The isomers were separated by injection of 8 mL aliquots onto a Chiral Pak AD preparative HPLC column (5×50 cm) (eluting with hexane/ethanol 7:3 at 70 mL/min with UV detection at 300 nm). The isomers were separated with the faster eluting diastereomer having a retention time of ~42 min (Diastereomer 1, Example 11) and the slower eluting diastereomer (Diastereomer 2, Example 12) having a retention time of ~50 min. The eluants were concentrated to provide the title compounds as white foams: Diastereomer 1 (1.14 g) and Diastereomer 2 (1.21 g).

Diastereomer 1: $^1$H NMR (500 MHz, acetone-d$_6$): 1.87 (s, 3H), 3.44–3.54 (m, 2H), 4.55 (t, 1H), 5.41 (br s, 1H), 6.91 (t, 1H), 6.94 (t, 1H), 7.13–7.18 (m, 3H), 7.22–7.26 (m, 3H), 7.33 (d, 1H), 7.41 (s, 1H), 7.50 (d, 2H), 7.55 (d, 1H), 7.79 (dd, 1H), 7.92 (d, 2H), 8.49 (s, 1H).

Diastereomer 2: $^1$H NMR (500 MHz, acetone-d$_6$): 1.87 (s, 3H), 3.42–3.54 (m, 2H), 4.56 (t, 1H), 5.45 (br s, 1H), 6.91 (t, 1H), 6.94 (t, 1H), 7.13–7.19 (m, 3H), 7.22–7.26 (m, 3H), 7.32 (d, 1H), 7.41 (s, 1H), 7.50 (d, 2H), 7.56 (d, 1H), 7.79 (dd, 1H), 7.92 (d, 2H), 8.49 (s, 1H).

Step 5: Mixture of Diastereomers 3 and 4 of 4-{2-[3,4-Bis(difluoromethoxy)phenyl]-2-{5-[2-(1-hydroxy-1-phenyl)ethyl]pyridyl}ethyl}pyridine N-oxide To a solution of Enantiomer 2 from Step 2 (207 mg, 0.4 mmol) in dichloromethane (10 mL) at −78° C. was added MeMgBr (2 mL of a 3M solution in ether) over 2 h. 25% NH$_4$OAc buffer was added and the mixture was extracted with dichloromethane. The organics were washed successively with water, brine, dried (MgSO$_4$), and concentrated. Flash chromatography of the residue (silica gel, dichloromethane/ethanol 95:5 to 92.5:7.5) provided the title compound as a white foam as a mixture of Diastereomers 3 and 4 (Example 13) (145 mg).

$^1$H NMR (500 MHz, acetone-d$_6$): 1.87 (s, 3H), 3.45–3.56 (m, 2H), 4.55 (t, 1H), 5.34 (br s, 1H), 6.91 (t, 1H), 6.93 (t, 1H), 7.13–7.17 (m, 3H), 7.23–7.26 (m, 3H), 7.33 (d, 1H), 7.41 (s, 1H), 7.49–7.51 (m, 2H), 7.55 (d, 1H), 7.79 (dd, 1H), 7.92 (d, 2H), 8.50 (s, 1H).

Example 11A

DIASTEREOMER 1 OF 4-{2-[3,4-BIS (DIFLUOROMETHOXY)PHENYL]-2-{5-[2-(1-HYDROXY-1-PHENYL)ETHYL] PYRIDYL}ETHYL}PYRIDINE N-OXIDE

Step 1: Enantiomers of 4-{2-[3,4-Bis (difluoromethoxy)phenyl]-2-[5-(2-carbomethoxy) pyridyl]ethyl}pyridine (±)-4-{2-[3,4-Bis(difluoromethoxy)phenyl]-2-[5-(2-carbomethoxy)pyridyl]ethyl}pyridine from Intermediate 2, Step 1 (12 g) was dissolved in ethanol/hexane (1:1, 36 mL). The isomers were separated by injection of 6 equal aliquots onto a Chiral Pak AD preparative HPLC column (5×50 cm) (eluting with hexane/ethanol 3:2 at 65 mL/min with UV detection at 290 nm). The enantiomers were separated, with the faster eluting enantiomer having a retention time of ~22 min (Enantiomer 1) and the slower eluting enantiomer (Enantiomer 2) having a retention time of ~36 min. The eluants containing Enantiomer 2 were concentrated to provide the compound as a brown gum (4.86 g).

Step 2: Optically Active 4-{2-[3,4-Bis (difluoromethoxy)phenyl]-2-[5-(2-N-methoxy-N-methylformamidyl)pyridyl]ethyl}pyridine Following the procedures described in Intermediate 2, Step 2, but substituting Enantiomer 2 from Step 1 above for racemic 4-{2-[3,4-bis(difluoromethoxy)phenyl]-2-[5-(2-carbomethoxy)pyridyl]ethyl}pyridine, the title product as an orange-brown gum.

Step 3: Optically Active 4-{2-[3,4-Bis(difluoromethoxy)phenyl]-2-[5-(2-benzoyl)pyridyl]ethyl}pyridine To a mechanically stirred solution amide from Step 2 (7 g, 14.6 mmol) in THF (100 mL) at −78° C. was added dropwise phenylmagnesium chloride. The mixture was stirred at −78° C. for 15 min, at −40° C. for 20 min and at 0° C. for 30 min. The mixture was poured into 25% NH$_4$OAc buffer (500 mL). The mixture was extracted with ethyl acetate three times, the organics were washed with water, dried (MgSO$_4$), and concentrated. Flash chromatography of the residue (silica gel, ethyl acetate/hexane 4:1) provided the title compound as a yellow oil (7.2 g).

Step 4: Optically Active 4-{2-[3,4-Bis(difluoromethoxy)phenyl]-2-[5-(2-benzoyl)pyridyl]ethyl}pyridine N-oxide Following the procedures described in Example 11, Step 1, but substituting optically active 4-{2-[3,4-bis(difluoromethoxy)phenyl]-2-[5-(2-benzoyl)pyridyl]ethyl}pyridine for (±)-4-{2-[3,4-Bis(difluoromethoxy)phenyl]-2-[5-(2-benzoyl)pyridyl]ethyl}pyridine, the title compound was obtained as a white foam.

Step 5: Diastereomer 1 of 4-{2-[3,4-Bis(difluoromethoxy)phenyl]-2-{5-[2-(1-hydroxy-1-phenyl)ethyl]pyridyl}ethyl}pyridine N-oxide The procedures described in Example 11, Steps 3 and 4 were followed using optically active 4-{2-[3,4-bis(difluoromethoxy)phenyl]-2-[5-(2-benzoyl)pyridyl]ethyl}pyridine N-oxide from Step 4 to provide the title compound as a white foam.

Example 14

(±/±)-4-{2-[3,4-BIS(DIFLUOROMETHOXY)PHENYL]-2-{5-[2-(1-HYDROXY-1-PHENYL)TRIFLUOROETHYL]PYRIDYL}ETHYL}PYRIDINE N-OXIDE

Step 1: (±/±)-4-{2-[3,4-Bis(difluoromethoxy)phenyl]-2-{5-[2-(1-hydroxy-1-phenyl)trifluoroethyl]pyridyl}ethyl}pyridine Following the procedures described in Example 6, but substituting (±)-4-{2-[3,4-bis(difluoromethoxy)phenyl]-2-[5-(2-benzoyl)pyridyl]ethyl}pyridine from Example 10, Step 1 (350 mg) for (±)-4-{2-[3,4-bis(difluoromethoxy)phenyl]-2-{5-[2-(1-keto-3-methyl)butyl]pyridyl}ethyl}pyridine N-oxide, and eluting with hexane/ethyl acetate (1:1) during flash chromatography, the title compound was obtained as an oil (250 mg).

Step 2: (±/±)-4-{2-[3,4-Bis(difluoromethoxy)phenyl]-2-{5-[2-(1-hydroxy-1-phenyl)trifluoroethyl]pyridyl}ethyl}pyridine N-oxide Following the procedures described in Example 10, Step 3 but substituting (±/±)-4-{2-[3,4-bis(difluoromethoxy)phenyl]-2-{5-[2-(1-hydroxy-1-phenyl)trifluoroethyl]pyridyl}ethyl}pyridine from Step 1 (250 mg) for (±/±)-4-{2-[3,4-bis(difluoromethoxy)phenyl]-2-{5-[2-(1-hydroxy-1-phenyl)ethyl]pyridyl}ethyl}pyridine, and eluting with ethyl acetate/methanol (9:1) during flash chromatography, the title compound was obtained as a white foam (180 mg).

$^1$H NMR (500 MHz, acetone-d$_6$): 3.53 (m, 2H), 4.66 (t, 1H), 6.87 (s, 1H), 6.92 (t, 1H), 6.94 (t, 1H), 7.17 (d, 2H), 7.27 (d, 1H), 7.34–7.39 (m, 4H), 7.43 (s, 1H), 7.61–7.65 (m, 3H), 7.91–7.97 (m, 3H), 8.64 (m, 1H).

Example 15

(±/±)-4-{2-[3,4-BIS(DIFLUOROMETHOXY)PHENYL]-2-{5-[2-(1-HYDROXY-1-PHENYL)PROPYL]PYRIDYL}ETHYL}PYRIDINE N-OXIDE

Following the procedures described in Example 10, Step 2 but substituting (±)-4-{2-[3,4-bis(difluoromethoxy)phenyl]-2-[5-(2-benzoyl)pyridyl]ethyl}pyridine N-oxide from Example 11, Step 1 for (±)-4-{2-[3,4-bis(difluoromethoxy)phenyl]-2-[5-(2-benzoyl)pyridyl]ethyl}pyridine and EtMgBr for MeMgCl, and eluting with ethyl acetate/ethanol (4:1) during flash chromatography, the title compound was obtained as a white foam (110 mg).

$^1$H NMR (500 MHz, acetone-d$_6$): 0.77 (t, 3H), 2.31 (q, 2H), 3.47 (m, 2H), 4.54 (t, 1H), 5.39 (1H), 6.91 (t, 1H), 6.93 (t, 1H), 7.16 (m, 3H), 7.25 (m, 3H), 7.32 (dd, 1H), 7.40 (d, 1H), 7.55 (m, 3H), 7.79 (m, 1H), 7.90 (d, 2H), 8.49 (dd, 1H).

Example 16

(±/±)-4-{2-[3,4-BIS(DIFLUOROMETHOXY)PHENYL]-2-{5-[2-(1-HYDROXY-1-PHENYL-2-METHYL)PROPYL]PYRIDYL}ETHYL}PYRIDINE N-OXIDE

Following the procedures described in Example 10, Step 2 but substituting (±)-4-{2-[3,4-bis(difluoromethoxy)phenyl]-2-[5-(2-benzoyl)pyridyl]ethyl}pyridine N-oxide from Example 1, Step 1 for (±)-4-{2-[3,4-bis(difluoromethoxy)phenyl]-2-[5-(2-benzoyl)pyridyl]ethyl}pyridine and i-PrMgBr for MeMgCl, and eluting with ethyl acetate/ethanol (4:1) during flash chromatography, the title compound was obtained as a white foam (180 mg).

$^1$H NMR (500 MHz, acetone-d6): 0.67 (d, 3H), 0.81 (d, 3H), 2.98 (m, 1H), 3.41–3.52 (m, 2H), 4.53 (t, 1H), 5.61 (1H), 6.75–7.07 (m, 2H), 7.13 (m, 3H), 7.22–7.27 (m, 3H), 7.30 (dd, 1H), 7.39 (s, 1H), 7.67 (m, 3H), 7.77–7.83 (m, 1H), 7.88–7.91 (m, 2H), 8.45–8.49 (m, 1H).

Example 17

(±)-4-{2-[3,4-BIS(DIFLUOROMETHOXY)PHENYL]-2-[5-(2-DIPHENYLCARBINOL)PYRIDYL]ETHYL}PYRIDINE N-OXIDE

Step 1: (±/±)-4-{2-[3,4-Bis(difluoromethoxy)phenyl]-2-[5-(2-diphenylcarbinol)pyridyl]ethyl}pyridine To a solution of (±)-4-{2-[3,4-bis(difluoromethoxy)phenyl]-2-[5-(2-benzoyl)pyridyl]ethyl}pyridine from Example 10, Step 1 (430 mg) in dichloromethane (15 mL) at −78° C. was added PhMgCl (0.7 mL of a 2M solution in THF). The mixture was stirred at −78° C. for 3 h and then sat. NH4Cl was added and the mixture was extracted with ether. The organics were washed with brine, dried (MgSO$_4$), and concentrated. Crystallization from ether followed by vigorous stirring in ether/hexane provided the title compound as a white solid (67 mg).

Step 2: (±)-4-{2-[3,4-Bis(difluoromethoxy)phenyl]-2-[5-(2-diphenylcarbinol)pyridyl]ethyl}pyridine N-oxide A mixture of (±)-4-{2-[3,4-bis(difluoromethoxy)phenyl]-2-[5-(2-diphenylcarbinol)pyridyl]ethyl}pyridine from Step 1 (67 mg) and MMPP (58 mg) in dichloromethane/methanol (3 mL, 9:1) was stirred at 25° C. for 4 h. The mixture was partitioned between sat. NaHCO$_3$ and ether and the organic phase was separated, washed with brine, dried (MgSO$_4$) and concentrated. Flash chromatography of the residue (silica gel; chloroform/methanol 95:5) provided the title compound as an oil (25 mg).

$^1$H NMR (500 MHz, acetone-d$_6$): 3.51 (m, 2H), 4.60 (t, 1H), 6.02 (s, 1H), 6.92 (t, 1H), 6.94 (t, 1H), 7.17 (d, 2H), 7.22–7.29 (m, 12H), 7.35 (m, 1H), 7.42 (s, 1H), 7.81 (m, 1H), 7.92 (m, 2H), 8.55 (s, 1H).

Example 18

(±/±)-4-{2-[3,4-BIS(DIFLUOROMETHOXY) PHENYL]-2-{5-[2-(1-HYDROXY-1-(3-FLUOROPHENYL))ETHYL] PYRIDYL}ETHYL}PYRIDINE N-OXIDE

Step 1: (±)-4-{2-[3,4-Bis(difluoromethoxy)phenyl]-2-[5-(2-(3-fluorobenzoyl))pyridyl]ethyl}pyridine Following the procedures described in Example 10, Step 1 but substituting m-fluorophenylmagnesium bromide for PhMgCl, and eluting with ethyl acetate/hexane (1:1) during flash chromatography, the title compound was obtained as an oil (230 mg).

Step 2: (±)-4-{2-[3,4-Bis(difluoromethoxy)phenyl]-2-[5-(2-(3-fluorobenzoyl))pyridyl]ethyl}pyridine N-oxide A mixture of (±)-4-{2-[3,4-bis(difluoromethoxy)phenyl]-2-[5-(2-(3-fluorobenzoyl))pyridyl]ethyl}pyridine from Step 1 (230 mg) and 80% mCPBA (116 mg) in chloroform (5 mL) was stirred at 0° C. for 3 h. Solid calcium hydroxide (120 mg) was added and after 15 min, the mixture was filtered. The filtrate was concentrated and flash chromatography of the residue (silica gel; ethyl acetate/methanol 9:1) provided the title compound as a white foam (181 mg).

Step 3: (±/±)-4- {2-[3,4-Bis(difluoromethoxy) phenyl]-2-{5-[2-(1-hydroxy-1-(3-fluorophenyl)) ethyl]pyridyl}ethyl}pyridine N-oxide To a solution of (±)-4-{2-[3,4-bis(difluoromethoxy) phenyl]-2-[5-(2-(3-fluorobenzoyl))pyridyl]ethyl}pyridine N-oxide from Step 2 (180 mg) in dichloromethane (15 mL) at 0° C. was added MeMgI (0.3 mL of a 3M solution in ether). The mixture was stirred at 0° C. for 1 h and then sat. NH$_4$Cl was added and the mixture was extracted with ether. The organics were washed with brine, dried (MgSO$_4$), and concentrated. Flash chromatography of the residue (silica gel; ethyl acetate/methanol 9:1) provided the title compound as a white foam (100 mg).

$^1$H NMR (400 MHz, acetone-d$_6$): 1.87 (s, 3H), 3.48 (m, 2H), 4.56 (t, 1H), 5.48 (s, 1H), 6.91 (t, 1H), 6.93 (t, 1H), 7.17 (m, 2H), 7.23–7.35 (m, 6H), 7.42 (s, 1H), 7.60 (d, 1H), 7.81 (m, 1H), 7.92 (d, 2H), 8.52 (s, 1H).

Example 19

(±/±)-4-{2-[3,4-BIS(DIFLUOROMETHOXY) PHENYL]-2-{5-[2-(1-HYDROXY-1-(4-FLUOROPHENYL))ETHYL] PYRIDYL}ETHYL}PYRIDINE N-OXIDE

Following the procedures described in Example 18 but substituting p-fluorophenylmagnesium bromide for m-fluorophenylmagnesium bromide, the title compound was obtained as a white foam (300 mg).

$^1$H NMR (500 MHz, acetone-d$_6$): 1.86 (s, 3H), 3.44–3.54 (m, 2H), 4.56 (t, 1H), 5.46 (1H), 6.77–7.10 (m, 4H), 7.17 (m, 2H), 7.25 (m, 1H), 7.33 (m, 1H), 7.41 (br s, 1H), 7.50–7.55 (m, 2H), 7.56 (d, 1H), 7.80 (m, 1H), 7.91 (m, 2H), 8.49 (t, 1H).

Example 20

(±/±)-4-{2-[3,4-BIS(DIFLUOROMETHOXY) PHENYL]-2-{5-[2-(1-HYDROXY-1-(4-CHLOROPHENYL))ETHYL] PYRIDYL}ETHYL}PYRIDINE N-OXIDE

Following the procedures described in Example 10 but substituting p-chlorophenylmagnesium bromide for phenylmagnesium chloride and MeMgI for MeMgCl, the title compound was obtained as a white foam (107 mg).

$^1$H NMR (500 MHz, acetone-d$_6$): 1.86 (s, 3H), 3.49 (m, 2H), 4.56 (t, 1H), 5.43 (s, 1H), 6.91 (t, 1H), 6.94 (t, 1H), 7.17 (m, 2H), 7.24–7.28 (m, 3H), 7.32 (m, 1H), 7.40 (s, 1H), 7.52 (m, 2H), 7.57 (d, 1H), 7.80 (m, 1H), 7.92 (m, 2H), 8.50 (s, 1H).

Examples 21–24

DIASTEREOMERS OF 4-{2-[3,4-BIS (DIFLUOROMETHOXY)PHENYL]-2-{5-[2-(1-HYDROXY-1-(4-CHLOROPHENYL))ETHYL] PYRIDYL}ETHYL}PYRIDINE N-OXIDE

Step 1: (±)-4-{2-[3,4-Bis(difluoromethoxy)phenyl]-2-[5-(2-(4-chlorobenzoyl)pyridyl]ethyl}pyridine Following the procedures described in Example 10, Step 1 but substituting p-chlorophenylmagnesium bromide for phenylmagnesium chloride, the title compound was obtained as a pale amber gum (1.14 g).

Step 2: (±)-4-{2-[3,4-Bis(difluoromethoxy)phenyl]-2-[5-(2-(4-chlorobenzoyl))pyridyl]ethyl}pyridine N-oxide Following the procedures described in Example 11, Step 1 but substituting (±)-4-{2-[3,4-bis(difluoromethoxy) phenyl]-2-[5-(2-(4-chlorobenzoyl))pyridyl]ethyl}pyridine from Step 1 (1.05 g) for (±)-4-{2-[3,4-bis(difluoromethoxy) phenyl]-2-[5-(2-benzoyl)pyridyl]ethyl}pyridine, and eluting with ethyl acetate/ethanol (85:15) during flash chromatography, the title compound was obtained as a white solid (949 mg).

Step 3: Separation of Enantiomers of 4-{2-[3,4-Bis (difluoromethoxy)phenyl]-2-[5-(2-(4-chlorobenzoyl))pyridyl]ethyl}pyridine N-oxide (±)-4-{2-[3,4-Bis(difluoromethoxy)phenyl]-2-[5-(2-(4-chlorobenzoyl))pyridyl]ethyl}pyridine N-oxide from Step 2 (620 mg) was dissolved in isopropanol/hexane (1:1, 10 mL). The enantiomers were separated by injection of 5 mL aliquots onto a Chiral Pak AD preparative HPLC column (5×50 cm) (eluting with hexane/isopropanol 4:1 at 75 mL/min with UV detection at 307 nm). The enantiomers were separated with the faster eluting enantiomer having a retention time of ~50 min (Enantiomer 1) and the slower eluting enantiomer (Enantiomer 2) having a retention time of ~61 min. The eluants were concentrated to provide the title compounds as white foams: Enantiomer 1 (271 mg) and Enantiomer 2 (247 mg).

Step 4: Mixture of Diastereomers 1 and 2 of 4-{2-[3,4-Bis(difluoromethoxy)phenyl]-2-[5-(2-(4-chlorobenzoyl))pyridyl]ethyl}pyridine N-oxide To a solution of Enantiomer 1 from Step 3 (248 mg, 0.45 mmol) in dichloromethane (10 mL) at −78° C. was added two portions of MeMgCl (7.9 mL of a 3M solution in THF) over 1 h. 25% NH$_4$OAc buffer (500 mL) was added and the mixture was extracted with dichloromethane. The organics were washed successively with water, brine, dried (MgSO$_4$), and concentrated. Flash chromatography of the residue (silica gel, ethyl acetate/ethanol 85:15) provided the title compound as a white foam (214 mg).

Step 5: Separation of Diastereomers 1 and 2 of 4-{2-[3,4-Bis(difluoromethoxy)phenyl]-2-[5-(2-(4-chlorobenzoyl))pyridyl]ethyl}pyridine N-oxide The mixture of 4-{2-[3,4-bis(difluoromethoxy)phenyl]-2-[5-(2-(4-chlorobenzoyl))pyridyl]ethyl}pyridine N-oxide diastereomers from Step 4 (180 mg) was dissolved in methanol/water (3:2, 4.5 mL). The isomers were separated by injection of 1.5 mL aliquots onto a Novapack C-18 preparative HPLC column (eluting with methanol/20 mM NH4OAc buffer (pH 5.4) 3:2 at 40 mL/min with UV detection at 287 nm). The isomers were separated with the faster eluting diastereomer having a retention time of ~14 min (Diastereomer 1, Example 21) and the slower eluting diastereomer (Diastereomer 2, Example 22) having a retention time of ~16 min. The eluants were concentrated to provide the title compounds as white foams: Diastereomer 1 (64 mg) and Diastereomer 2 (73 mg).

Diastereomer 1: $^1$H NMR (500 MHz, acetone-d$_6$): 1.86 (s, 3H), 3.48 (m, 2H), 4.57 (t, 1H), 5.39 (s, 1H), 6.91 (t, 1H), 6.93 (t, 1H), 7.18 (d, 2H), 7.27 (m, 3H), 7.32 (d, 1H), 7.40 (s, 1H), 7.51 (d, 2H), 7.57 (d, 1H), 7.80 (dd, 1H), 7.91 (d, 2H), 8.49 (s, 1H).

Diastereomer 2: $^1$H NMR (500 MHz, acetone-d$_6$): 1.86 (s, 3H), 3.52 (m, 2H), 4.58 (t, 1H), 5.48 (s, 1H), 6.91 (t, 1H), 6.94 (t, 1H), 7.20–7.28 (m, 5H), 7.32 (d, 1H), 7.40 (s, 1H), 7.51 (d, 2H), 7.58 (d, 1H), 7.81 (dd, 1H), 8.01 (d, 2H), 8.50 (s, 1H).

Step 6: Mixture of Diastereomers 3 and 4 of 4-{2-[3,4-Bis(difluoromethoxy)phenyl]-2-[5-(2-(4-chlorobenzoyl))pyridyl]ethyl}pyridine N-oxide Following the procedures described in Step 4 but substituting Enantiomer 2 from Step 3 (218 mg) for Enantiomer 1, the title compound was obtained as a white solid (152 mg).

Step 7: Separation of Diastereomers 3 and 4 of 4-{2-[3,4-Bis(difluoromethoxy)phenyl]-2-[5-(2-(4-chlorobenzoyl))pyridyl]ethyl}pyridine N-oxide The mixture of 4-{2-[3,4-bis(difluoromethoxy)phenyl]-2-[5-(2-(4-chlorobenzoyl))pyridyl]ethyl}pyridine N-oxide diastereomers from Step 6 (180 mg) was dissolved in methanol/water (3:2, 4.5 mL). The isomers were separated by injection of 1.5 mL aliquots onto a Novapack C-18 preparative HPLC column (eluting with methanol/20 mM NH$_4$OAc buffer (pH 5.4) 3:2 at 40 mL/min with UV detection at 287 nm). The isomers were separated with the faster eluting diastereomer having a retention time of ~14 min (Diastereomer 3, Example 23) and the slower eluting diastereomer (Diastereomer 4, Example 24) having a retention time of ~16 min. The eluants were concentrated to provide the title compounds as white foams: Diastereomer 3 (51 mg) and Diastereomer 4 (55 mg).

Example 25

(±/±)-4-{2-[3,4-BIS(DIFLUOROMETHOXY)PHENYL]-2-{5-[2-(1-HYDROXY-1-(2-METHYLPHENYL))TRIFLUOROETHYL]PYRIDYL}ETHYL}PYRIDINE N-OXIDE

Step 1: (±)-4-{2-[3,4-Bis(difluoromethoxy)phenyl]-2-[5-(2-(2-methylbenzoyl))pyridyl]ethyl}pyridine To a solution of Intermediate 1 (665 mg, 1.58 mmol) in dichloromethane (15 mL) at 0° C. was added o-tolylmagnesium bromide (2.4 mL of a 2M solution in ether, 4.7 mmol) dropwise. After 2 h at 25° C., 25% NH$_4$OAc was added and the mixture extracted three times with dichloromethane. The combined organics were washed with brine, dried (MgSO$_4$) and concentrated. Flash chromatography of the residue (silica gel; ethanol/dichloromethane 5:95) provided the intermediate secondary alcohol (750 mg). To a solution of oxalyl chloride (190 mL) in dichloromethane (8 mL) at −78° C. was added dimethylsulfoxide (248 mL)and the mixture was stirred for 15 min. A solution of the secondary alcohol in dichloromethane (8 mL)was added and then, after 15 min, triethyl amine (1.02 mL) was added. The mixture was stirred at −78° C. for 5 min and then at 25° C. for 30 min. 25% NH$_4$OAc was added and the mixture extracted with dichloromethane. The organics were washed with brine, dried (MgSO$_4$) and concentrated. Flash chromatography of the residue (silica gel; ethyl acetate/hexane 7:3 to 100% ethyl acetate) provided the title compound as a colorless oil (724 mg).

Step 2: (±)-4-{2-[3,4-Bis(difluoromethoxy)phenyl]-2-[5-(2-(2-methylbenzoyl))pyridyl]ethyl}pyridine N-oxide Following the procedures described in Example 11, Step 1 but substituting (±)-4-{2-[3,4-bis(difluoromethoxy)phenyl]-2-[5-(2-(2-methylbenzoyl))pyridyl]ethyl}pyridine from Step 1 (724 mg) for (±)-4-{2-[3,4 -bis(difluoromethoxy)phenyl]-2-[5-(2-benzoyl)pyridyl]ethyl}pyridine, and eluting with dichloromethane/ethanol (95:5 to 85:15) during flash chromatography, the title compound was obtained as a white foam (652 mg).

Step 3: (±/±)-4-{2-[3,4-Bis(difluoromethoxy)phenyl]-2-{5-[2-(1-hydroxy-1-(2-methylphenyl))trifluoroethyl]pyridyl}ethyl}pyridine N-oxide Following the procedures described in Example 6, but substituting (±)-4-{2-[3,4-bis(difluoromethoxy)phenyl]-2-[5-(2-(2-methylbenzoyl))pyridyl]ethyl}pyridine N-oxide from Step 2 (440 mg) for (±)-4-{2-[3,4-bis(difluoromethoxy)phenyl]-2-{5-[2-(1-keto-3-methyl)butyl]pyridyl}ethyl}pyridine N-oxide, and eluting with dichloromethane/ethanol (95:5 to 93:7) during flash chromatography, the title compound was obtained as a white foam (262 mg).

$^1$H NMR (300 MHz, acetone-d$_6$): 1.70 (s, 3H), 3.51–3.58 (m, 2H), 4.67 (t, 1H), 6.94 (app dt, 2H), 7.11–7.19 (m, 4H), 7.23–7.30 (m, 3H), 7.37 (d, 1H), 7.43 (s, 1H), 7.67 (m, 1H), 7.85–7.93 (m, 3H), 8.65 (d, 1H).

Example 26

(±/±)-4-{2-[3,4-BIS(DIFLUOROMETHOXY)PHENYL]-2-{5-[2-(1-HYDROXY-1-(3-METHYLPHENYL))TRIFLUOROETHYL]PYRIDYL}ETHYL}PYRIDINE N-OXIDE

Following the procedures described in Example 25, but substituting m-tolylmagnesium chloride for o-tolylmagnesium bromide, the title compound was obtained as a beige foam (247 mg).

$^1$H NMR (400 MHz, acetone-d$_6$): 2.31 (s, 3H), 3.54 (m, 2H), 4.67 (t, 1H), 6.93 (t, 1H), 6.95 (t, 1H), 7.16–7.20 (m, 3H), 7.24–7.28 (m, 2H), 7.36 (dd, 1H), 7.41–7.47 (m, 3H), 7.61 (d, 1H), 7.90–7.97 (m, 3H), 8.65 (dd, 1H).

Example 27

(±/±)-4-{2-[3,4-BIS(DIFLUOROMETHOXY) PHENYL]-2-{5-[2-(1-HYDROXY-1-(4-METHYLPHENYL))TRIFLUOROETHYL] PYRIDYL}ETHYL}PYRIDINE N-OXIDE

Following the procedures described in Example 25, but substituting p-tolylmagnesium bromide for o-tolylmagnesium bromide, the title compound was obtained as a white foam (332 mg).

$^1$H NMR (500 MHz, acetone-d$_6$): 2.29 (s, 3H), 3.49–3.58 (m, 2H), 4.66 (t, 1H), 6.92 (t, 1H), 6.94 (t, 1H), 7.15–7.19 (m, 4H), 7.27 (d, 1H), 7.36 (dd, 1H), 7.44 (s, 1H), 7.50 (d, 2H), 7.59 (d, 1H), 7.91–7.97 (m, 3H), 8.64 (dd, 1H).

Example 28

(±/±)-4-{2-[3,4-BIS(DIFLUOROMETHOXY) PHENYL]-2-{5-[2-(1-HYDROXY-1-(4-ETHYLPHENYL))TRIFLUOROETHYL] PYRIDYL}ETHYL}PYRIDINE N-OXIDE

Following the procedures described in Example 25, but substituting p-ethylphenylmagnesium bromide for o-tolylmagnesium bromide, the title compound was obtained as an off-white foam (213 mg).

$^1$H NMR (500 MHz, acetone-d$_6$): 1.19 (t, 3H), 2.61 (m, 2H), 3.54 (m, 2H), 4.66 (t, 1H), 6.76 (s, 1H), 6.92 (t, 1H), 6.94 (t, 1H), 7.18 (d, 2H), 7.22 (m, 2H), 7.27 (d, 1H), 7.36 (m, 1H), 7.44 (s, 1H), 7.53 (d, 2H), 7.60 (d, 1H), 7.91–7.97 (m, 3H), 8.65 (m, 1H).

Example 29

(±/±)-4-{2-[3,4-BIS(DIFLUOROMETHOXY) PHENYL]-2-{5-[2-(1-HYDROXY-1-(4-METHYLSULFONYLPHENYL))ETHYL] PYRIDYL}ETHYL}PYRIDINE N-OXIDE

Step 1: (±)-4-{2-[3,4-Bis(difluoromethoxy)phenyl]-2-[5-(2-(4-methylthiobenzoyl))pyridyl] ethyl}pyridine To a solution of 4-bromothioanisole (318 mg, 1.57 mmol) in THF (4 mL) at −78° C. was added n-BuLi (0.65 mL of a 2.4M solution in hexane). After 25 min, a solution of Intermediate 2 (625 mg, 1.3 mmol) in THF (3 mL) was added. The mixture was stirred at −78° C. for 3 h and was then slowly allowed to warm to 25° C. over 1.5 h. 25% NH$_4$OAc buffer was added and the mixture was extracted with ethyl acetate. The organics were washed with brine, dried (MgSO$_4$), and concentrated. Flash chromatography of the residue (silica gel, ethyl acetate/hexane 1:4) provided the title compound as a yellow gum (160 mg).

Step 2: (±)-4-{2-[3,4-Bis(difluoromethoxy)phenyl]-2-[5-(2-(4-methylsulfonolbenzoyl))pyridyl] ethyl}pyridine N-oxide Following the procedures described in Example 11, Step 1 but substituting (±)-4-{2-[3,4-bis(difluoromethoxy) phenyl]-2-[5-(2-(4 -methylthiobenzoyl))pyridyl] ethyl}pyridine from Step 1 (159 mg) for (±)-4-{2-[3,4-bis (difluoromethoxy)phenyl]-2-[5-(2-benzoyl)pyridyl] ethyl}pyridine, the title compound was obtained as a pale yellow solid (155 mg).

Step 3: (±/±)-4-{2-[3,4-Bis(difluoromethoxy) phenyl]-2-{5-[2-(1-hydroxy-1-(4-methylsulfonylphenyl))ethyl]pyridyl}ethyl}pyridine N-oxide To a solution of (±)-4-{2-[3,4-bis(difluoromethoxy) phenyl]-2-[5-(2-(4-methylsulfonylbenzoyl))pyridyl] ethyl}pyridine N-oxide from Step 2 (154 mg, 0.26 mmol) in dichloromethane (4 mL) at −78° C. was added MeMgBr (0.43 mL of a 3M solution in ether). The mixture was stirred at −78° C. for 6 h and then 25% NH$_4$OAc buffer was added and the mixture was extracted with ethyl acetate. The organics were washed with brine, dried (MgSO$_4$), and concentrated. Flash chromatography of the residue (silica gel, dichloromethane/methanol 95:5) provided the title compound as a white foamy solid (79 mg).

$^1$H NMR (500 MHz, acetone-d$_6$): 1.91 (s, 3H), 3.06 (s, 3H), 3.50 (m, 2H), 4.57 (m, 1H), 6.91 (t, 1H), 6.93 (t, 1H), 7.15 (m, 2H), 7.25 (m, 1H), 7.33 (m, 1H), 7.40 (s, 1H), 7.64 (m, 1H), 7.77–7.84 (m, 5H), 7.90 (m, 2H), 8.51 (m, 1H).

Example 30

(±/±)-4-{2-[3,4-BIS(DIFLUOROMETHOXY) PHENYL]-2-{5-[2-(1-HYDROXY-1-(2-THIAZOLYL))ETHYL] PYRIDYL}ETHYL}PYRIDINE N-OXIDE

Step 1: (±)-4-{2-[3,4-Bis(difluoromethoxy)phenyl]-2-[5-(2-(2-ketothiazolyl))pyridyl]ethyl}pyridine To a solution of thiazole (0.13 mL, 1.77 mmol) in THF (20 mL) at −78° C. was added n-BuLi (0.74 mL of a 2.4M solution in hexane). After 40 min, a solution of Intermediate 2 (425 mg, 0.89 mmol) in THF (10 mL) was added dropwise. The mixture was stirred at −78° C. for 1 h and then 25% NH$_4$OAc buffer was added. The mixture was extracted with ethyl acetate, the organics were washed with brine, dried (MgSO$_4$), and concentrated. Flash chromatography of the residue (silica gel, chloroform/ethanol 95:5) provided the title compound as a beige gum (435 mg).

Step 2: (±)-4-{2-[3,4-Bis(difluoromethoxy)phenyl]-2-[5-(2-(2-ketothiazolyl))pyridyl]ethyl}pyridine N-oxide Following the procedures described in Example 11, Step 1 but substituting (±)-4-{2-[3,4-bis(difluoromethoxy) phenyl]-2-[5-(2-(2-ketothiazolyl))pyridyl]ethyl}pyridine from Step 1 (418 mg,) for (±)-4-{2-[3,4-bis (difluoromethoxy)phenyl]-2-[5-(2-benzoyl)pyridyl] ethyl}pyridine, the title compound was obtained as an off-white foam (229 mg).

Step 3: (±/±)-4-{2-[3,4-Bis(difluoromethoxy) phenyl]-2-{5-[2-(1-hydroxy-1-(2-thiazolyl))ethyl] pyridyl}ethyl}pyridine N-oxide Following the procedures described in Example 29, Step 3 but substituting (±)-4-{2-[3,4-bis(difluoromethoxy) phenyl]-2-[5-(2-(4-methylsulfonylbenzoyl))pyridyl] ethyl}pyridine N-oxide from Step 2 (109 mg) for (±)-4-{2-[3,4-bis(difluoromethoxy)phenyl]-2-[5-(2-(4- methylsulfonylbenzoyl))pyridyl]ethyl}pyridine N-oxide, the title compound was obtained as a pale yellow foam (62 mg).

$^1$H NMR (400 MHz, acetone-d$_6$): 1.88 (s, 3H), 3.51 (m, 2H), 4.61 (t, 1H), 6.44 (s, 1H), 6.92 (m, 2H), 7.17–7.20 (m, 2H), 7.25 (m, 1H), 7.34 (m, 1H), 7.42–7.45 (m, 2H), 7.69 (m, 1H), 7.45 (m, 1H), 7.89–7.95 (m, 3H), 8.52 (m, 1H).

Example 31

(±/±)-4-{2-[3,4-BIS(DIFLUOROMETHOXY) PHENYL]-2-{5-[2-(1-HYDROXY-1-(2-THIAZOLYL))TRIFLUOROETHYL] PYRIDYL}ETHYL}PYRIDINE N-OXIDE

Following the procedures described in Example 6, but substituting (±)-4-{2-[3,4-bis(difluoromethoxy)phenyl]-2-[5-(2-(2-ketothiazolyl))pyridyl]ethyl}pyridine N-oxide from Example 30, Step 2 (114 mg) for (±)-4-{2-[3,4-bis (difluoromethoxy)phenyl]-2-{5-[2-(1-keto-3-methyl)butyl] pyridyl}ethyl}pyridine N-oxide, and eluting with chloroform/ethanol (95:5 to 92:8) during flash chromatography, the title compound was obtained as a pale yellow foam (77 mg).

$^1$H NMR (500 MHz, acetone-d6): 3.56 (m, 2H), 4.71 (m, 1H), 6.93 (m, 2H), 7.20 (d, 2H), 7.27 (m, 1H), 7.37 (m, 1H), 7.47 (d, 2H), 7.71 (m, 1H), 7.90–7.94 (m, 3H), 8.09 (m, 1H), 8.19 (m, 1H), 8.68 (m, 1H).

Example 32

CHIRAL 4-{2-[(3-CYCLOBUTYLOXY-4-DIFLUOROMETHOXY) PHENYL]-2-{5-[2-(1-HYDROXY-1-METHYL)ETHYL] PYRIDYL}ETHYL}PYRIDINE N-OXIDE

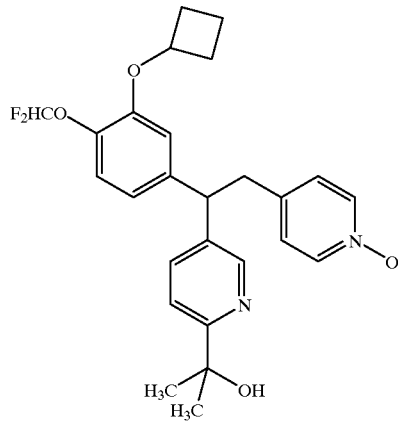

Step 1: (±)-(3-Cyclobutyloxy-4-difluoromethoxy) phenyl-5-(2-bromo)pyridylcarbinol To a solution of 2,5-dibromopyridine (20.0 g, 84.2 mmol) in anhydrous ether at −78° C. was added n-BuLi (53 mL of a 1.6 M solution in hexane, 84.2 mmol) over 10 min. After 30 min, 3-cyclobutyloxy-4-difluoromethoxybenzaldehyde (17.0 g, 70.2 mmol) in anhydrous ether (100 mL) was added via cannula over 5 min. The mixture was stirred at −78° C. for 20 min and then the temperature was slowly raised to −40° C. over 50 min. The mixture was poured into saturated ammonium chloride (300 mL) and extracted thrice with ethyl acetate. The organic layer was washed with brine, dried (MgSO$_4$) and concentrated. Flash chromatography of the residue (silica gel; ethyl acetate/hexane 30:70 to 50:50) yielded (±)-(3-Cyclobutyloxy-4-difluoromethoxy)phenyl-5-(2-bromo)pyridylcarbinol as a yellow oil (27.5 g).

Step 2: (±)-4-{2-[(3-Cyclobutyloxy-4-difluoromethoxy)phenyl]-2-[5-(2-bromo)pyridyl] ethyl}pyridine To a solution of (±)-(3-cyclobutyloxy-4-difluoromethoxy) phenyl-5-(2-bromo)pyridylcarbinol from Step 1 (20.2 g, 50.5 mmol) in dichloromethane (430 mL) at 25° C. was added thionyl chloride (4.78 mL, 65.6 mmol) and the resulting mixture was stirred at this temperature for 35 min. The mixture was carefully poured into 5% NaHCO$_3$ (500 mL), the phases were separated and the aqueous phase extracted with dichloromethane. The combined organics were washed with 5% NaHCO$_3$, brine, dried (Na$_2$SO$_4$) and concentrated to provide the crude chloride as an orange-brown oil (21.0 g) that was used immediately.

To a solution of ethyl 4-pyridylacetate (23.2 mL, 151 mmol) in THF (630 mL) and HMPA (26.3 mL, 151 mmol) at 25° C. was added potassium bis(trimethylsilyl)amide (303 mL of a 0.5M solution in toluene, 151 mmol). The resulting mixture was stirred for 30 min and then a THF (170 mL) solution of the chloride prepared above was added over 15 min and then stirred for 2 h at 25° C. The mixture was poured into sat. NH$_4$Cl (1.2 L) and extracted twice with ethyl acetate. The combined organics were washed successively with 25% NH$_4$OAc buffer, brine, dried (Na$_2$SO$_4$) and concetrated to give a thick brown oil. This material was dissolved in a mixture of THF/MeOH/water (3:1:1, 1.1 L), 2N LiOH (227 mL, 454 mmol) was added and the mixture was stirred at 25° C. for 15 h. 6N HCl (81 mL) was slowly added and the mixture was stirred for 45 min. The volatiles were removed on the rotovap and the residue was partitioned between sat. NaHCO$_3$ and ethyl acetate. The aqueous phase was extracted twice with ethyl acetate and the combined organics were washed successively with 25% NH$_4$OAc buffer, water, brine, dried (Na$_2$SO$_4$) and concetrated to give a orange-brown gum. Flash chromatography (silica gel; ethyl acetate/hexane 4:1 to 100% ethyl acetate) yielded (±)-4-{2-[(3-Cyclobutyloxy-4-difluoromethoxy)phenyl]-2-[5-(2-bromo)pyridyl]ethyl}pyridine as a yellow gum (21.5 g).

Step 3: (±)-4-{2-[(3-Cyclobutyloxy-4-difluoromethoxy)phenyl]-2-[5-(2-carbomethox) pyridyl]ethyl}pyridine Argon was bubbled through a 0° C. solution of (±)-4-{2-[(3-cyclobutyloxy-4-difluoromethoxy)phenyl]-2-[5-(2-bromo)pyridyl]ethyl}pyridine from Step 2 (10.6 g, 22.4 mmol) in DMF (25 mL) and MeOH (25 mL) for 10 min. The cooling bath was removed and palladium(II) acetate (151 mg, 0.67 mmol), dppf (744 mg, 1.34 mmol), triethylamine (6.24 mL, 44.7 mmol) were added successively. The mixture was evacuated under reduced pressure and then placed under an atmosphere of CO (1 atm, balloon) and heated at 60° C. for 20 h. The mixture was cooled to 25° C. and the volatiles were removed in vacuo. The residue was partitioned between water (200 mL) and ethyl acetate and the aqueous phase was extracted with ethyl acetate. The combined organics were washed twice with water, dried (Na$_2$SO$_4$) and concetrated. Flash chromatography of the residue (silica gel; acetone/ethyl acetate 1:4 to 3:7) yielded (±)-4-{2-[(3-Cyclobutyloxy-4-difluoromethoxy)phenyl]-2-[5-(2-carbomethoxy)pyridyl]ethyl}pyridine as a brown gum (9.3 g).

Step 4: Resolution of (±)-4-{2-[(3-Cyclobutyloxy-4-difluoromethoxy)phenyl]-2-[5-(2-carbomethoxy) pyridyl]ethyl}pyridine A solution of (±)-4-{2-[(3-cyclobutyloxy-4-difluoromethoxy)phenyl]-2-[5-(2-carbomethoxy)pyridyl]

ethyl}pyridine (Step 3; 9.17 g) in isopropanol/hexane (43 mL, 1.3:1) was injected (4×2.3 g) onto a chiralpack AD preparative (5 cm×50 cm) HPLC column (eluting with hexane/ethanol 6:4 at 70 mL/min with UV detection at 300 nm). The enantiomers were separated with the faster eluting enantiomer having a retention time of ~21 min (Enantiomer 1) and the slower eluting enantiomer (Enantiomer 2) having a retention time of ~31 min. The eluants were concentrated to provide the enantiomers as brown gums: Enantiomer 1 (4.32 g) and Enantiomer 2 (4.25 g).

Step 5: Chiral 4-{2-[(3-Cyclobutyloxy-4-difluoromethoxy)phenyl]-2-[5-(2-carbomethoxy)pyridyl]ethyl}pyridine N-oxide To a solution of chiral 4-{2-[(3-cyclobutyloxy-4-difluoromethoxy)phenyl]-2-[5-(2-carbomethoxy)pyridyl]ethyl}pyridine (Enantiomer 2 from Step 4) (4.24 g, 9.33 mmol) in dichloromethane/methanol (176 mL, 10:1) at 25° C. was added MMPP (9.23 g, 18.6 mmol). After stirring for 4.5 h, the mixture was poured into 5% NaHCO$_3$ (500 mL) and the mixture was extracted with chloroform. The organics were washed with 5% NaHCO$_3$, water, dried (Na$_2$SO$_4$) and concentrated. Flash chromatography of the residue (silica gel; chloroform/ethanol 9:1 to 86:14) yielded Chiral 4-{2-[(3-Cyclobutyloxy-4-difluoromethoxy)phenyl]-2-[5-(2-carbomethoxy)pyridyl]ethyl}pyridine N-oxide as an off-white foam (3.0 g).

Step 6: Chiral 4-{2-[(3-Cyclobutyloxy-4-difluoromethoxy)phenyl]-2-{5-[2-(1-hydroxy-1-methyl)ethyl]pyridyl}ethyl}pyridine N-oxide To a solution of chiral 4-{2-[(3-cyclobutyloxy-4-difluoromethoxy)phenyl]-2-[5-(2-carbomethoxy)pyridyl]ethyl}pyridine N-oxide from Step 5 (2.71 g, 5.76 mmol) in dichloromethane (90 mL) at −78° C. was added MeMgBr (9.6 mL of a 3M solution in ether). The mixture was stirred at −78° C. for 25 min, warmed to −20° C. over 30 min, and then stirred at this temperature for 30 min. The mixture was poured into 25% NH$_4$OAc buffer (300 mL) and the mixture was extracted with chloroform. The organics were washed with 25% NH$_4$OAc buffer, brine, dried (Na$_2$SO$_4$), and concentrated. The crude mixture was submitted a second time to the same reaction conditions and, after work-up, flash chromatography of the residue (silica gel, ethanol/chloroform 1:9 to 1:4) yielded Chiral 4-{2-[(3-Cyclobutyloxy-4-difluoromethoxy)phenyl]-2-{5-[2-(1-hydroxy-1-methyl)ethyl]pyridyl}ethyl}pyridine N-oxide as a white foam (2.19 g).

$^1$H NMR (500 MHz, acetone-d$_6$): 1.43 (s, 6H), 1.60–1.70 (m, 1H), 1.77–1.84 (m, 1H), 2.00–2.14 (m, 2H), 2.36–2.47 (m, 2H), 3.47 (m, 2H), 4.48 (t, 1H), 4.60 (s, 1H), 4.75 (quintet, 1H), 6.80 (t, 1H), 6.94–6.99 (m, 2H), 7.07 (d, 1H), 7.16 (d, 2H), 7.56 (d, 1H), 7.80 (dd, 1H), 7.93 (d, 2H), 8.48 (d, 1H).

Example 33

CHIRAL 4-{2-[(3-CYCLOBUTYLOXY-4-DIFLUOROMETHOXY)PHENYL]-2-{5-[2-(1-HYDROXY-1-METHYL)ETHYL]PYRIDYL}ETHYL}PYRIDINE N-OXIDE HYDROCHLORIDE SALT

To a solution of chiral 4-{2-[(3-cyclobutyloxy-4-difluoromethoxy)phenyl]-2-{5-[2-(1-hydroxy-1-methyl)ethyl]pyridyl}ethyl}pyridine N-oxide from Example 32, Step 6 (2.18 g, 4.63 mmol) in ethyl acetate (40 mL) at 25° C. was added HCl (4.63 mL of a 1.0M solution in ether, 4.63 mmol) and the mixture was stirred for 10 min, forming an off-white precipitate. The ethyl acetate was removed in vacuo and the residue was dried under high vacuum for 10 min. The residue was triturated and sonicated in anhydrous ether, resulting in a suspension that was stirred for 1 h. The ether was decanted and replaced with fresh ether. This procedure was repeated before concentrating and drying under high vacuum. The title compound was obtained as a beige solid (2.23 g).

H NMR (500 MHz, acetone-d$_6$): 1.58 (s, 6H), 1.60–1.70 (m, 1H), 1.77–1.83 (m, 1H), 2.00–2.17 (m, 2H), 2.39–2.48 (m, 2H), 3.77 (m, 2H), 4.74–4.82 (m, 2H), 6.82 (t, 1H), 7.02–7.11 (m, 3H), 7.60 (d, 2H), 7.84 (d, 1H), 8.24 (d, 1H), 8.41 (d, 2H), 8.67 (s, 1H).

Example 34

CHIRAL 4-{2-[(3-CYCLOPROPYLOXY-4-DIFLUOROMETHOXY)PHENYL]-2-{5-[2-(1-HYDROXY-1-METHYL)ETHYL]PYRIDYL}ETHYL}PYRIDINE N-OXIDE

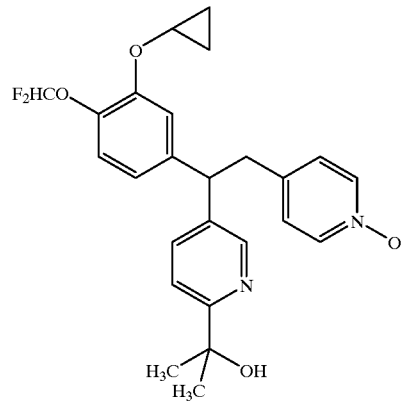

Step 1: (±)-(3-Cyclopronyloxy-4-difluoromethoxy)phenyl-5-{2-[1-(2-(trimethylsilyl)ethoxvmehtyloxy-1-methyl]ethyl}pyridylcarbinol To a solution of 5-bromo-2-(1-hydroxy-1-methyl)ethyl pyridine (600 mg, 1.74 mmol) in anhydrous THF at −100° C. was added n-BuLi (1.08 mL of a 1.6M solution in hexane, 1.74 mmol). After 20 min, 3-cyclopropyloxy-4-difluoromethoxybenzaldehyde (330 mg, 1.45 mmol) in anhydrous THF (2 mL) was added via cannula. The resulting mixture was stirred at −78° C. for 2 h, quenched with saturated ammonium chloride, and diluted with ethyl acetate and a 25% solution of ammonium acetate. The aqueous layer was extracted with ethyl acetate and the combined organic layers were then washed with brine, dried (MgSO$_4$) and concentrated. Flash chromatography of the residue (silica gel; ethyl acetate/hexane 40:60) provided (±)-(3-Cyclopropyloxy-4-difluoromethoxy)phenyl-5-{2-[1-(2-(trimethylsilyl)ethoxymehtyloxy-1-methyl]ethyl}pyridylcarbinol as an oil (718 mg, 100%).

Step 2: (±)-4-{2-[(3-Cyclopropyloxy-4-difluoromethoxy)phenyl]-2-{5-{2-[1-(2-(trimethylsilyl)ethoxymethyloxy-1-methyl]ethyl}pyridyl}ethyl}pyridine (±)-(3-Cyclopropyloxy-4-difluoromethoxy)phenyl-5-{2-[1-(2-(trimethylsilyl)ethoxymethyloxy-1-methyl]ethyl}pyridylcarbinol from Step 1 (718 mg, 1.44 mmol) in toluene (2.5 mL) at 25° C. was cannulated to a solution of thionyl chloride (0.127 mL, 1.74 mmol) and pyridine (0.291 mL, 3.6 mmol) in 5.0 mL of toluene. The resulting mixture was stirred at this temperature for 1 h, poured directly on a silica gel column and eluted with ethyl acetate/toluene (20:80) to yield 652 mg of chloride that was used immediately.

To a solution of ethyl 4-pyridylacetate (628 mg, 3.8 mmol) in THF (14 mL) and HMPA (0.661 mL, 3.8 mmol) at 0° C. was added potassium bis(trimethylsilyl)amide (7.6 mL of a 0.5M solution in toluene, 3.8 mmol). The resulting mixture was stirred for 30 min and then a THF (4.0 mL) solution of the chloride prepared above was added and then stirred for 16 h at 25° C. The reaction was quenched with saturated ammonium chloride and diluted with ethyl acetate and a 25% solution of ammonium acetate. The aqueous layer was extracted with ethyl acetate and the combined organic layers were washed with brine, dried ($MgSO_4$) and concentrated. This material was dissolved in a mixture of THF/MeOH/water (3:1:1, 28 mL), 2N LiOH (5.7 mL, 11.4 mmol) was added and the mixture was stirred at 60° C. for 2 h. 2N HCl (5.7 mL) was slowly added at 25° C. and the volatiles were removed on the rotovap. The residue was partitioned between 25% $NH_4OAc$ buffer and ethyl acetate. The aqueous phase was extracted with ethyl acetate and the combined organics were washed with brine, and dried ($MgSO_4$). Flash chromatography (silica gel; ethyl acetate/hexane 80:20 to 100% ethyl acetate) provided (±)-4-{2-[(3-Cyclopropyloxy-4-difluoromethoxy)phenyl]-2-{5-{2-[1-(2-(trimethylsilyl)ethoxymethyloxy-1-methyl]ethyl}pyridyl}ethyl}pyridine as an oil (710 mg, 86%).

Step 3: (±)-4-{2-[(3-Cyclopropyloxy-4-difluoromethoxy)phenyl]-2-{5-{2-[1-(2-(trimethylsilyl)ethoxymethyloxy-1-methyl]ethyl}pyridyl}ethyl}pyridine-N-oxide To a solution of (±)-4-{2-[(3-cyclopropyloxy-4-difluoromethoxy)phenyl]-2-{5-{2-[1-(2-(trimethylsilyl)ethoxymethyloxy-1-methyl]ethyl}pyridyl}ethyl}pyridine (from Step 4) (710 mg, 1.24 mmol) in dichloromethane/methanol (22.0 mL, 10:1) at 25° C. was added MMPP (614 mg, 1.24 mmol). After stirring for 1.5 h, the mixture was poured directly on a silica gel column and eluted with EtOH/dichloromethane (15% to 20%) to yield 573 mg of (±)-4-{2-[(3-Cyclopropyloxy-4-difluoromethoxy)phenyl]-2-{5-{2-[1-(2-(trimethylsilyl)ethoxymethyloxy-1-methyl]ethyl}pyridyl}ethyl}pyridine-N-oxide contaminated with the starting material and the regioisomeric N-oxides.

Step 4: (±)-4-{2-[(3-Cyclopropyloxy-4-difluoromethoxy)phenyl]-2-{5-[2-(1-hydroxy-1-methyl)ethyl]pyridyl}ethyl}pyridine-N-oxide To a 0° C. solution of (±)-4-{2-[(3-cyclopropyloxy-4-difluoromethoxy)phenyl]-2-{5-{2-[1-(2-(trimethylsilyl)ethoxymethyloxy-1-methyl]ethyl}pyridyl}ethyl}pyridine-N-oxide (573 mg, mixture from Step 3) in dichloromethane (10 mL), was added 1.0 mL of trifluoroacetic acid. The resulting solution was stirred 30 minutes at 0° C. and 30 minutes at 25° C. and diluted with a mixture of ethyl acetate/25% ammonium acetate buffer. The aqueous layer was extracted twice with ethyl acetate while the combined organic layers were washed with brine and dried over ($MgSO_4$). Flash chromatography (silica gel; EtOH/dichloromethane 30:70) provided (±)-4-{2-[(3-Cyclopropyloxy-4-difluoromethoxy)phenyl]-2-{5-[2-(1-hydroxy-1-methyl)ethyl]pyridyl}ethyl}pyridine-N-oxide as a white foam (305 mg, 53% for 2 steps).

Step 5: Resolution of (±)-4-{2-[(3-Cyclopropyloxy-4-difluoromethoxy)phenyl]-2-{5-[2-(1-hydroxy-1-methyl)ethyl]pyridyl}ethyl}pyridine-N-oxide A solution of (±)-4-{2-[(3-Cyclopropyloxy-4-difluoromethoxy)phenyl]-2-{5-[2-(1-hydroxy-1-methyl)ethyl]pyridyl}ethyl}pyridine-N-oxide (Step 4; 250 mg) in ethanol/hexane (5 mL, 30:70) was injected onto a chiralpack AD preparative (5 cm×50 cm) HPLC column (eluting with ethanol/hexane 30:70 at 80 mL/min with UV detection at 290 nm). The enantiomers were separated with the faster eluting enantiomer having a retention time of ~27 min (Enantiomer 1) and the slower eluting enantiomer (Enantiomer 2) having a retention time of ~41 min. The eluants were concentrated to provide the enantiomers as a white foam: Enantiomer 1 (100 mg) and Enantiomer 2 (100 mg).

$^1$H NMR (500 MHz, acetone-$d_6$): 8.5 (s, 1H), 7.95 (d, 2H), 7.42 (dd, 1H), 7.58 (d, 1H), 7.47 (s, 1H), 7.19 (d, 2H), 7.07 (d, 1H), 6.98 (d, 1H), 6.73 (t, 1H), 4.6 (s, 1H), 4.51 (t, 1H), 3.92–3.87 (m, 1H), 3.55–3.44 (m, 2H), 1.44 (s, 6H), 0.86–0.61 (m, 4H).

What is claimed is:

1. A compound represented by formula I:

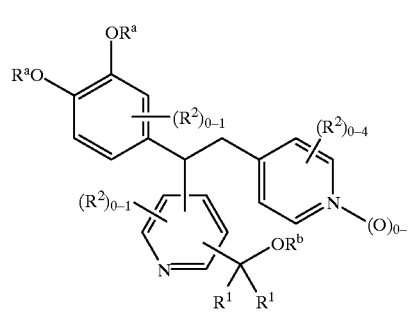

or a pharmaceutically acceptable salt thereof wherein:

each $R^a$ independently represents a member selected from the group consisting of H, $C_{1-6}$alkyl and halo$C_{1-6}$alkyl;

$R^b$ represents a member selected from the group consisting of H, $C_{1-6}$alkyl, halo$C_{1-6}$alkyl;

each $R^1$ independently represents a member selected from the group consisting of: $C_{1-10}$alkyl, aryl, heteroaryl, substituted $C_{1-10}$alkyl, substituted aryl and substituted heteroaryl, wherein the substituents are 1–6 members selected from the group consisting of $C_{1-4}$alkyl, halo, hydroxy, halo$C_{1-4}$alkyl, CN, $C_{1-4}$alkoxy, $C_{1-4}$alkylthio, $C_{1-4}$alkyl-$SO_2$— and $H_2NSO_2$—; and when present, each $R^2$ independently represents a member selected from the group consisting of halo, $C_{1-6}$alkyl, halo$C_{1-6}$alkyl and CN.

2. A compound in accordance with claim 1 represented by Formula Ia:

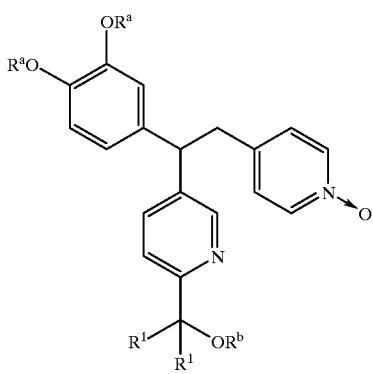

wherein all variables are as originally defined.

3. A compound in accordance with claim 1 wherein each $R^a$ represents difluoromethyl and $R^b$ represents H.

4. A compound in accordance with claim 2 wherein each $R^a$ represents difluoromethyl and $R^b$ represents H.

5. A compound in accordance with claim 1 wherein one $R^1$ group represents alkyl and the other represents aryl or substituted aryl.

6. A compound in accordance with claim 2 wherein one $R^1$ group represents alkyl and the other represents aryl or substituted aryl.

7. A compound in accordance with claim 1 wherein each $R^1$ represents methyl and one $R^a$ represents cycloalkoxy.

8. A compound in accordance with claim 7 wherein one $R^a$ represents cyclobutyloxy or cyclopropyloxy.

9. A compound in accordance with claim 2 wherein each $R^1$ represents methyl and one $R^a$ represents cycloalkoxy.

10. A compound in accordance with claim 9 wherein one $R^a$ represents cyclobutyloxy or cyclopropyloxy.

11. A compound according to claim 1 which is a single diastereoisomer.

12. A compound according to claim 1 which is a single optical isomer.

13. A compound according to claim 1 in which each $R^a$ is difluoromethyl, $R^b$ is H, one $R^1$ is methyl, one $R^1$ is phenyl and the N-oxide is present.

14. A compound according to claim 13 which is a single optical isomer, or a pharmaceutically acceptable salt or hydrate thereof.

15. A compound in accordance with claim 1 selected from (a) through (hh) below:

(a) (±)-4-{2-[3,4-Bis(difluoromethoxy)phenyl]-2-{5-[2-(1-hydroxy-1-methyl)ethyl]pyridyl}ethyl}pyridine N-oxide, (b and c) Optical isomers of 4-{2-[3,4-Bis (difluoromethoxy)phenyl]-2-{5-[2-(1-hydroxy-1-methyl)ethyl]pyridyl}ethyl}pyridine N-oxide, (d) (±)-4-{2-[3,4-Bis(difluoromethoxy)phenyl]-2-{5-[2-(1-ethyl-1-hydroxy)propyl]pyridyl}ethyl}pyridine N-oxide, (e) (±/±)-4-{2-[3,4-Bis(difluoromethoxy)phenyl]-2-{5-[2-(1-hydroxy-1-isobutyl)ethyl]pyridyl}ethyl}pyridine N-oxide, (f) (±/±)-4-{2-[3,4-Bis(difluoromethoxy)phenyl]-2-{5-[2-(1-hydroxy-1-isobutyl)trifluoroethyl]pyridyl}ethyl}pyridine N-oxide, (g) (±/±)-4-{2-[3,4-Bis(difluoromethoxy)phenyl]-2-{5-[2-(1-hydroxy-1-methyl)pentyl]pyridyl}ethyl}pyridine N-oxide, (h) (±/±)-4-{2-[3,4-Bis(difluoromethoxy)phenyl]-2-{5-[2-(1-cyclohexyl-1-hydroxy)ethyl]pyridyl}ethyl}pyridine N-oxide, (i) (±/±)-4-{2-[3,4-Bis(difluoromethoxy)phenyl]-2-{5-[2-(1-cyclohexyl-1-hydroxy)trifluoroethyl]pyridyl}ethyl}pyridine N-oxide, (j) (±/±)-4-{2-[3,4-Bis(difluoromethoxy)phenyl]-2-{5-[2-(1-hydroxy-1-phenyl)ethyl]pyridyl}ethyl}pyridine N-oxide, (k,l and m) Optical isomers of 4-{2-[3,4-Bis (difluoromethoxy)phenyl]-2-{5-[2-(1-hydroxy-1-phenyl)ethyl]pyridyl}ethyl}pyridine N-oxide, (n) (±/±)-4-{2-[3,4-Bis(difluoromethoxy)phenyl]-2-{5-[2-(1-hydroxy-1-phenyl)trifluoroethyl]pyridyl}ethyl}pyridine N-oxide, (o) (±/±)-4-{2-[3,4-Bis(difluoromethoxy)phenyl]-2-{5-[2-(1-hydroxy-1-phenyl)propyl]pyridyl}ethyl}pyridine N-oxide, (p) (±/±)-4-{2-[3,4-Bis(difluoromethoxy)phenyl]-2-{5-[2-(1-hydroxy-1-phenyl-2-methyl)propyl]pyridyl}ethyl}pyridine N-oxide, (q) (±)-4-{2-[3,4-Bis(difluoromethoxy)phenyl]-2-[5-(2-diphenylcarbinol)pyridyl]ethyl}pyridine N-oxide, (r) (±/±)-4-{2-[3,4-Bis(difluoromethoxy)phenyl]-2-{5-[2-(1-hydroxy-1-(3-fluorophenyl))ethyl]pyridyl}ethyl}pyridine N-oxide, (s) (±/±)-4-{2-[3,4-Bis(difluoromethoxy)phenyl]-2-{5-[2-(1-hydroxy-1-(4-fluorophenyl))ethyl]pyridyl}ethyl}pyridine N-oxide, (t) (±/±)-4-{2-[3,4-Bis(difluoromethoxy)phenyl]-2-{5-[2-(1-hydroxy-1-(4-chlorophenyl))ethyl]pyridyl}ethyl}pyridine N-oxide, (u to x) Optical isomers of 4-{2-[3,4-Bis (difluoromethoxy)phenyl]-2-{5-[2-(1-hydroxy-1-(4-chlorophenyl))ethyl]pyridyl}ethyl}pyridine N-oxide, (y) (±/±)-4-{2-[3,4-Bis(difluoromethoxy)phenyl]-2-{5-[2-(1-hydroxy-1-(2-methylphenyl))trifluoroethyl]pyridyl}ethyl}pyridine N-oxide, (z) (±/±)-4-{2-[3,4-Bis(difluoromethoxy)phenyl]-2-{5-[2-(1-hydroxy-1-(3-methylphenyl))trifluoroethyl]pyridyl}ethyl}pyridine N-oxide, (aa) (±/±)-4-{2-[3,4-Bis(difluoromethoxy)phenyl]-2-{5-[2-(1-hydroxy-1-(4-methylphenyl))trifluoroethyl]pyridyl}ethyl}pyridine N-oxide, (bb) (±/±)-4-{2-[3,4-Bis(difluoromethoxy)phenyl]-2-{5-[2-(1-hydroxy-1-(4-ethylphenyl))trifluoroethyl]pyridyl}ethyl}pyridine N-oxide, (cc) (±/±)-4-{2-[3,4-Bis(difluoromethoxy)phenyl]-2-{5-[2-(1-hydroxy-1-(4-methylsulfonylphenyl))ethyl]pyridyl}ethyl}pyridine N-oxide, (dd) (±/±)-4-{2-[3,4-Bis(difluoromethoxy)phenyl]-2-{5-[2-(1-hydroxy-1-(2-thiazolyl))ethyl]pyridyl}ethyl}pyridine N-oxide, (ee) (±/±)-4-{2-[3,4-Bis(difluoromethoxy)phenyl]-2-{5-[2-(1-hydroxy-1-(2-thiazolyl))trifluoroethyl]pyridyl}ethyl}pyridine N-oxide, (ff) chiral 4-{2-[(3-Cyclobutyloxy-4-difluoromethoxy)phenyl]-2-{5-[2-(1-hydroxy-1-methyl)ethyl]pyridyl}ethyl}pyridine N-oxide, (gg) chiral 4-{2-[(3-Cyclobutyloxy-4-difluoromethoxy)phenyl]-2-{5-[2-(1-hydroxy-1-methyl)ethyl]pyridyl}ethyl}pyridine N-oxide hydrochloride salt, and (hh) chiral 4-{2-[(3-Cyclopropyloxy-4-difluoromethoxy)phenyl]-2-{5-[2-(1-hydroxy-1-methyl)ethyl]pyridyl}ethyl}pyridine-N-oxide.

16. A compound in accordance with claim 1 in accordance with the following table:

TABLE 1

Ib

[Structure: F$_2$HCO and OCHF$_2$ substituted phenyl attached to a carbon bearing a CH$_2$-pyridyl-N-oxide group and a pyridyl group with C(R$^{1a}$)(R$^{1b}$)OH substituent]

| Example | R$^{1a}$ | R$^{1b}$ |
|---|---|---|
| 1 | CH$_3$ | CH$_3$ |
| 2* | CH$_3$ | CH$_3$ |
| 3* | CH$_3$ | CH$_3$ |
| 4 | Et | CH$_2$CH$_3$ |
| 5 | i-Bu | CH$_3$ |
| 6 | i-Bu | CF$_3$ |
| 7 | n-Bu | CH$_3$ |
| 8 | c-Hex | CH$_3$ |
| 9 | c-Hex | CF$_3$ |
| 10 | Phenyl | CH$_3$ |
| 11 | Phenyl | CH$_3$ |
| 12* | Phenyl | CH$_3$ |
| 13* | Phenyl | CH$_3$ |
| 14 | Phenyl | CF$_3$ |
| 15 | Phenyl | CH$_2$CH$_3$ |
| 16 | Phenyl | i-Pr |
| 17 | Phenyl | Phenyl |
| 18 | m-F-Phenyl | CH$_3$ |
| 19 | p-F-Phenyl | CH$_3$ |
| 20 | p-Cl-Phenyl | CH$_3$ |
| 21* | p-Cl-Phenyl | CH$_3$ |
| 22* | p-Cl-Phenyl | CH$_3$ |
| 23* | p-Cl-Phenyl | CH$_3$ |
| 24* | p-Cl-Phenyl | CH$_3$ |
| 25 | o-CH$_3$-Phenyl | CF$_3$ |
| 26 | m-CH$_3$-Phenyl | CF$_3$ |
| 27 | p-CH$_3$-Phenyl | CF$_3$ |
| 28 | p-Et-Phenyl | CF$_3$ |
| 29 | p-MeSO$_2$-Phenyl | CH$_3$ |
| 30 | 2-Thiazolyl | CH$_3$ |
| 31 | 2-Thiazolyl | CF$_3$ |
| 35* | p-OH-phenyl | CH$_3$ | or a pharmaceutically acceptable salt or hydrate thereof, wherein Me is methyl, Et is ethyl, c-Hex is cyclohexyl, n-Bu is n-butyl and i-Bu is isobutyl.

17. A compound according to claim 1, selected from chiral 4-{2-[(3-Cyclobutyloxy-4-difluoromethoxy)phenyl]-2-{5-[2-(1-hydroxy-1-methyl)ethyl]pyridyl}ethyl}pyridine N-oxide or a pharmaceutically acceptable salt thereof.

18. A compound according to claim 1, selected from chiral 4-{2-[(3-Cyclopropyloxy-4-difluoromethoxy)phenyl]-2-{5-[2-(1-hydroxy-1-methyl)ethyl]pyridyl}ethyl}pyridine-N-oxide or a pharmaceutically acceptable salt thereof.

19. A pharmaceutical composition comprising a compound in accordance with claim 1 in combination with a pharmaceutically acceptable carrier.

20. A method of treating or preventing a PDE IV mediated disease or condition in a mammalian patient in need of such treatment or prevention, comprising administering to said patient an amount of a compound in accordance with claim 1 that is effective for treating or preventing said PDE IV mediated disease or condition.

21. A method in accordance with claim 20 wherein the PDE IV mediated disease or condition is selected from the group consisting of:

bladder or alimentary smooth muscle spasm;

asthma, cystic fibrosis, chronic bronchitis or inflammatory adult respiratory distress syndrome;

eosinophilic granuloma, psoriasis, or another benign or malignant proliferative skin disease;

endotoxic shock, septic shock, ulcerative colitis, Crohn's disease, or reperfusion injury of the myocardium or brain;

inflammatory arthritis, chronic glomerulonephritis, atopic dermatitis or urticaria;

diabetes, alzheimer's disease, allergic rhinitis, allergic conjunctivitis, vernal conjunctivitis, arterial restenosis or atherosclerosis;

neurogenic inflammation;

rheumatoid arthritis, multiple sclerosis, ankylosing spondylitis, transplant rejection or graft versus host disease;

bacterial, fungal or viral induced sepsis and septic shock;

rheumatoid or osteoarthritis;

cancer, tumor growth or metastasis;

cachexia; and depression or memory impairment.

22. A method in accordance with claim 21 wherein the PDE IV mediated disease or condition is asthma, cystic fibrosis, chronic bronchitis or inflammatory adult respiratory distress syndrome.

* * * * *